United States Patent [19]

Sherts

[11] Patent Number: 5,728,113

[45] Date of Patent: Mar. 17, 1998

[54] ENDOSCOPIC VASCULAR SUTURING APPARATUS

[75] Inventor: Charles R. Sherts, Southport, Conn.

[73] Assignee: United States Surgical Corporation, Norwalk, Conn.

[21] Appl. No.: 662,943

[22] Filed: Jun. 12, 1996

Related U.S. Application Data

[63] Continuation of Ser. No. 319,840, Oct. 7, 1994, abandoned.

[51] Int. Cl.$^6$ .................................................. A61B 17/00
[52] U.S. Cl. ..................... 606/145; 606/139; 606/147; 112/169
[58] Field of Search ............................ 606/139, 144, 606/145, 147, 148, 151, 205–208; 112/169, 80.03

[56] References Cited

U.S. PATENT DOCUMENTS

| | | | |
|---|---|---|---|
| 984,756 | 2/1911 | Frisch | 606/207 |
| 1,037,864 | 9/1912 | Carlson et al. | |
| 1,131,163 | 3/1915 | Saunders et al. | |
| 1,293,565 | 2/1919 | Smit | |
| 1,449,087 | 3/1923 | Bugbee | |
| 1,876,792 | 6/1932 | Thompson | |
| 2,213,830 | 9/1940 | Anastasi | |
| 2,880,728 | 4/1959 | Rights | |
| 3,073,311 | 1/1963 | Tibbs et al. | |

(List continued on next page.)

FOREIGN PATENT DOCUMENTS

| | | | |
|---|---|---|---|
| 0 482 881 | 4/1992 | European Pat. Off. | |
| 535906 | 4/1993 | European Pat. Off. | 606/148 |
| 0 601 676 A2 | 6/1994 | European Pat. Off. | |
| 0 647 431 A2 | 4/1995 | European Pat. Off. | |
| 0647431 | 12/1995 | European Pat. Off. | |
| 337579 | 9/1904 | France | |
| 91 09 097 | 10/1991 | Germany | |
| 41 24 383 C1 | 5/1992 | Germany | |
| 41 24 381 C1 | 8/1992 | Germany | |
| 41 27 812 | 2/1993 | Germany | |
| 41 39 628 C1 | 3/1993 | Germany | |
| 1103-854 | 7/1984 | U.S.S.R. | |
| 1505-514 | 9/1989 | U.S.S.R. | |
| 1725847-A1 | 4/1992 | U.S.S.R. | |
| 586661 | 3/1947 | United Kingdom | |
| 914298 | 3/1947 | United Kingdom | |
| 1249853 | 10/1971 | United Kingdom | |
| 2260704 | 4/1993 | United Kingdom | |
| WO 93/01750 | 2/1993 | WIPO | |

OTHER PUBLICATIONS

European Search Report.
"Surgeon's Stitch Gun Never Releases Needle," Design in Action, vol. 905 Machine Design 55 (1962,63,)5, 117.
Aesculap Catalog, p. 401 (Date: 1905).

*Primary Examiner*—Jeffrey A. Schmidt

[57] ABSTRACT

An endoscopic apparatus for suturing vascular tissue including a body portion having a first and a second jaw mounted for movement on a distal end thereon and moveable between an open position spaced apart to a closed position wherein the first and second jaws are in close cooperative alignment and a handle member for moving the first and second jaws to move them between the open and closed positions. The apparatus further includes a reciprocating mechanism associated with the first and second jaws and movable between a first position securing a surgical needle within the first jaw and a second position releasing the surgical needle from the first jaw and a cam actuating lever engagable with the reciprocating mechanism such that the cam actuating lever cams the reciprocating mechanism between the first and second positions in response to predetermined movement of the handle member.

30 Claims, 23 Drawing Sheets

U.S. PATENT DOCUMENTS

| | | | |
|---|---|---|---|
| 3,090,386 | 5/1963 | Curtis . | |
| 3,349,772 | 10/1967 | Rygg . | |
| 3,470,875 | 10/1969 | Johnson . | |
| 3,807,407 | 4/1974 | Schweizer . | |
| 3,842,840 | 10/1974 | Schweizer . | |
| 3,901,244 | 8/1975 | Schweizer . | |
| 3,946,740 | 3/1976 | Bassett . | |
| 4,021,896 | 5/1977 | Stierlein . | |
| 4,109,658 | 8/1978 | Hughes . | |
| 4,161,951 | 7/1979 | Scanlan, Jr. . | |
| 4,164,225 | 8/1979 | Johnson et al. . | |
| 4,236,470 | 12/1980 | Stenson . | |
| 4,345,601 | 8/1982 | Fukuda . | |
| 4,373,530 | 2/1983 | Kilejian . | |
| 4,471,781 | 9/1984 | Di Giovanni et al. . | |
| 4,491,135 | 1/1985 | Klein . | |
| 4,580,567 | 4/1986 | Schweitzer et al. . | |
| 4,621,640 | 11/1986 | Mulhollan et al. . | |
| 4,635,638 | 1/1987 | Weintraub et al. | 606/205 |
| 4,827,931 | 5/1989 | Longmore | 606/148 |
| 4,890,615 | 1/1990 | Caspari et al. . | |
| 4,923,461 | 5/1990 | Caspari et al. . | |
| 4,935,027 | 6/1990 | Yoon . | |
| 4,957,498 | 9/1990 | Caspari et al. . | |
| 4,983,176 | 1/1991 | Cushman et al. | 606/151 |
| 5,059,201 | 10/1991 | Asnis . | |
| 5,100,421 | 3/1992 | Christoudias . | |
| 5,171,257 | 12/1992 | Ferzli . | |
| 5,188,636 | 2/1993 | Fedotov . | |
| 5,207,693 | 5/1993 | Phillips . | |
| 5,217,471 | 6/1993 | Burkhart . | |
| 5,224,948 | 7/1993 | Abe et al. . | |
| 5,242,458 | 9/1993 | Bendel et al. . | |
| 5,254,126 | 10/1993 | Filipi et al. . | |
| 5,261,917 | 11/1993 | Hasson et al. . | |
| 5,281,220 | 1/1994 | Blake, III . | |
| 5,300,082 | 4/1994 | Sharpe et al. . | |
| 5,336,191 | 8/1994 | Davis et al. . | |
| 5,389,103 | 2/1995 | Melzer et al. | 606/147 |
| 5,454,823 | 10/1995 | Richardson et al. . | |
| 5,474,057 | 12/1995 | Makower et al. | 606/205 |

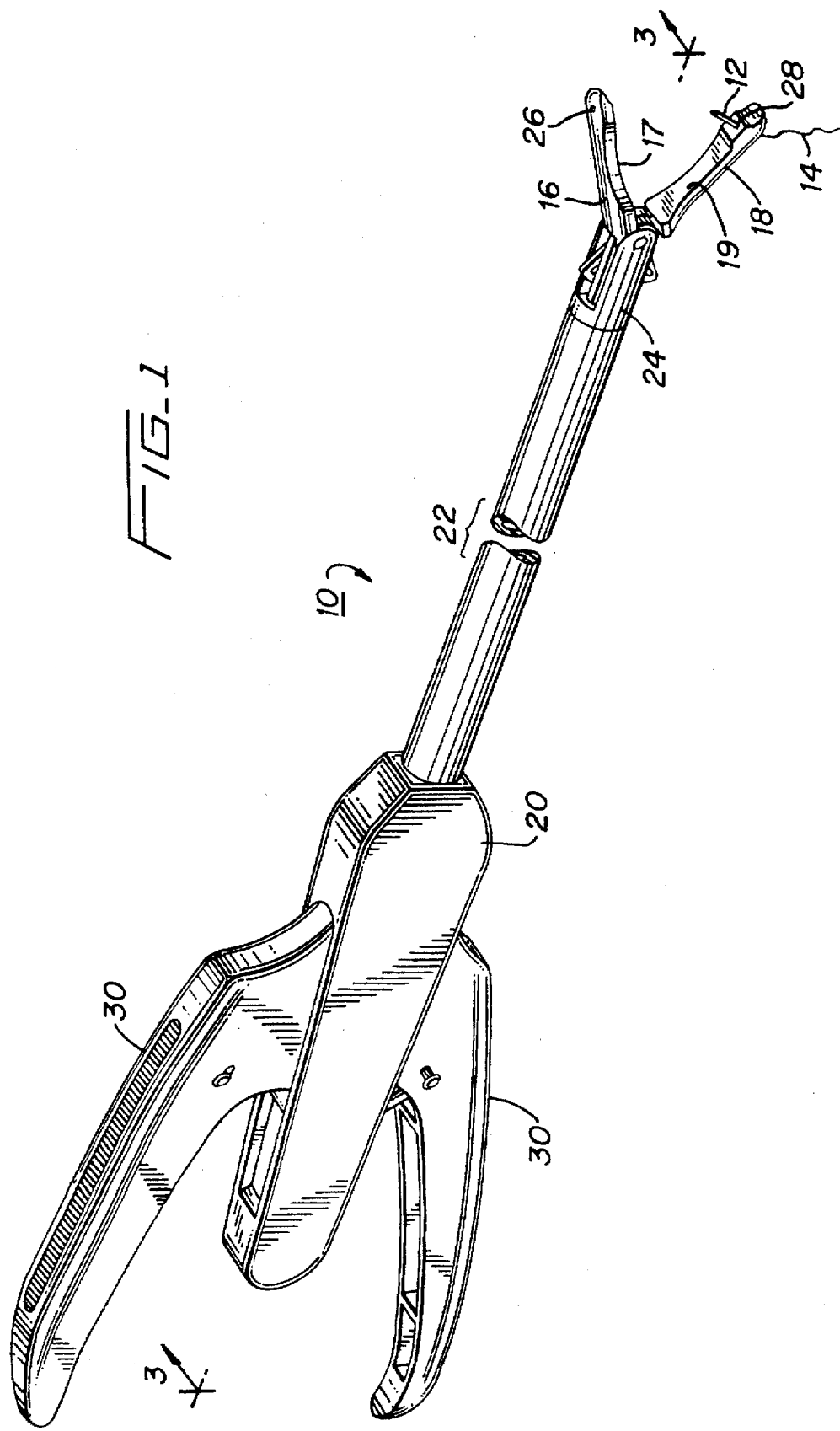

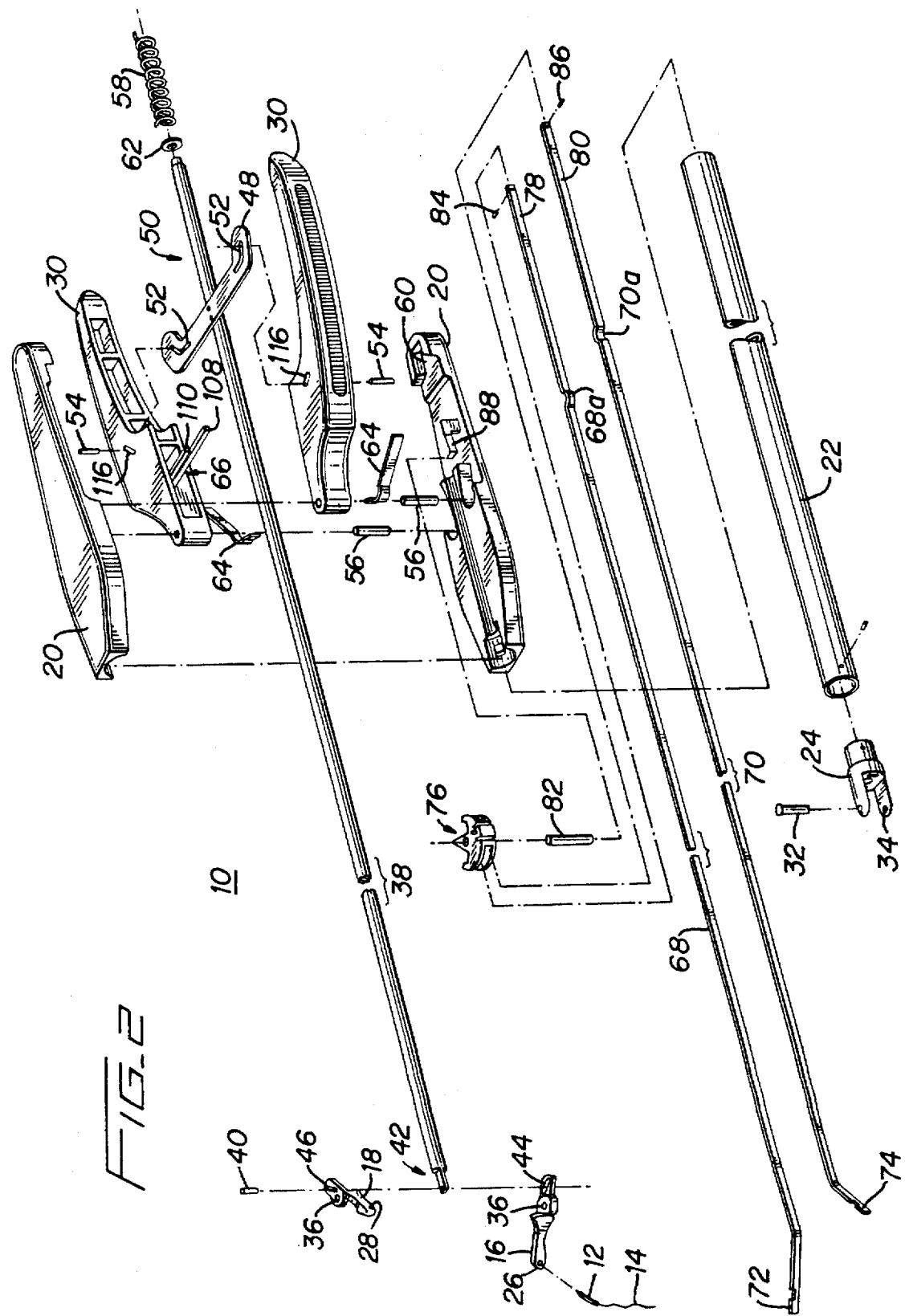

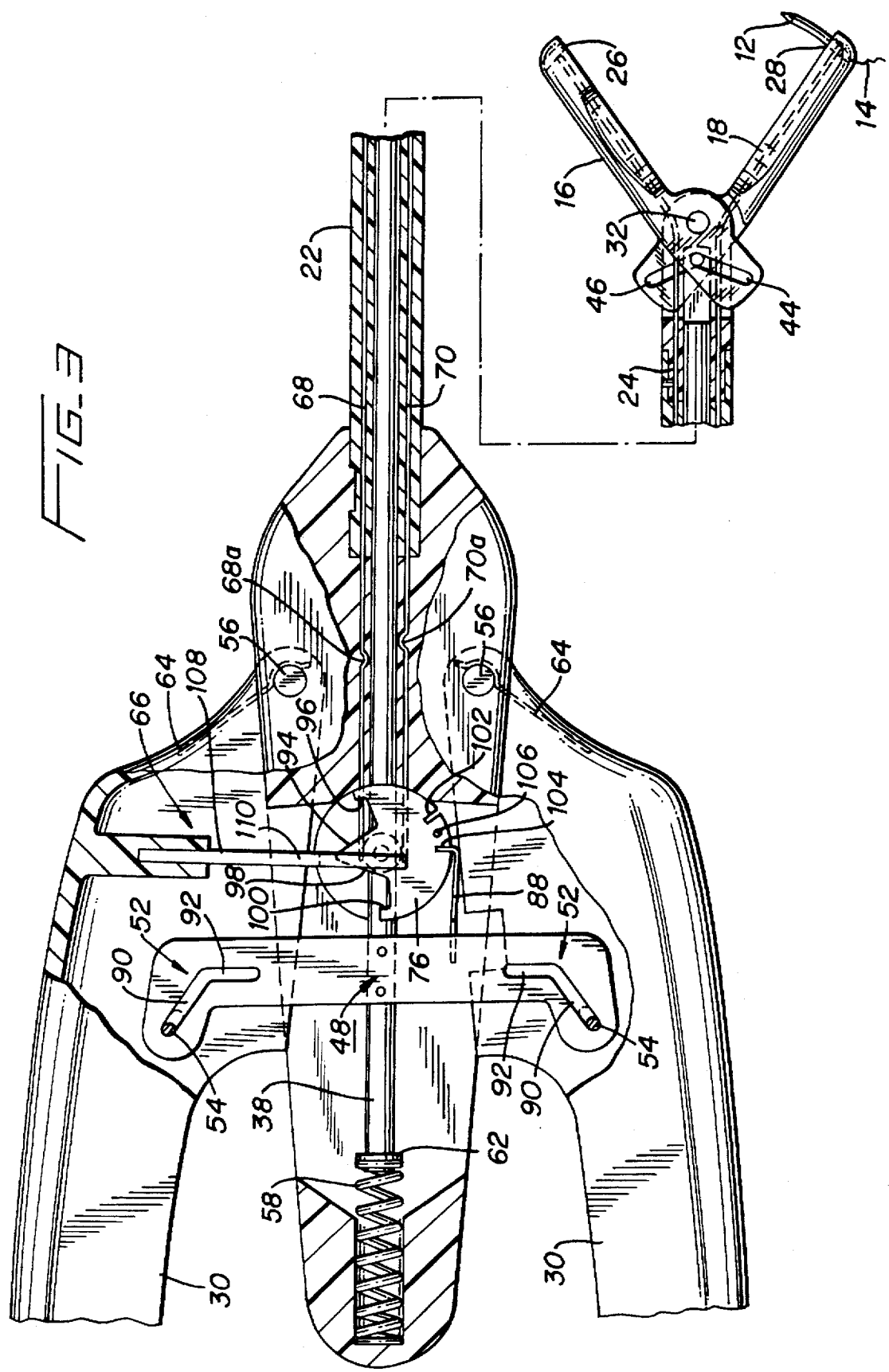

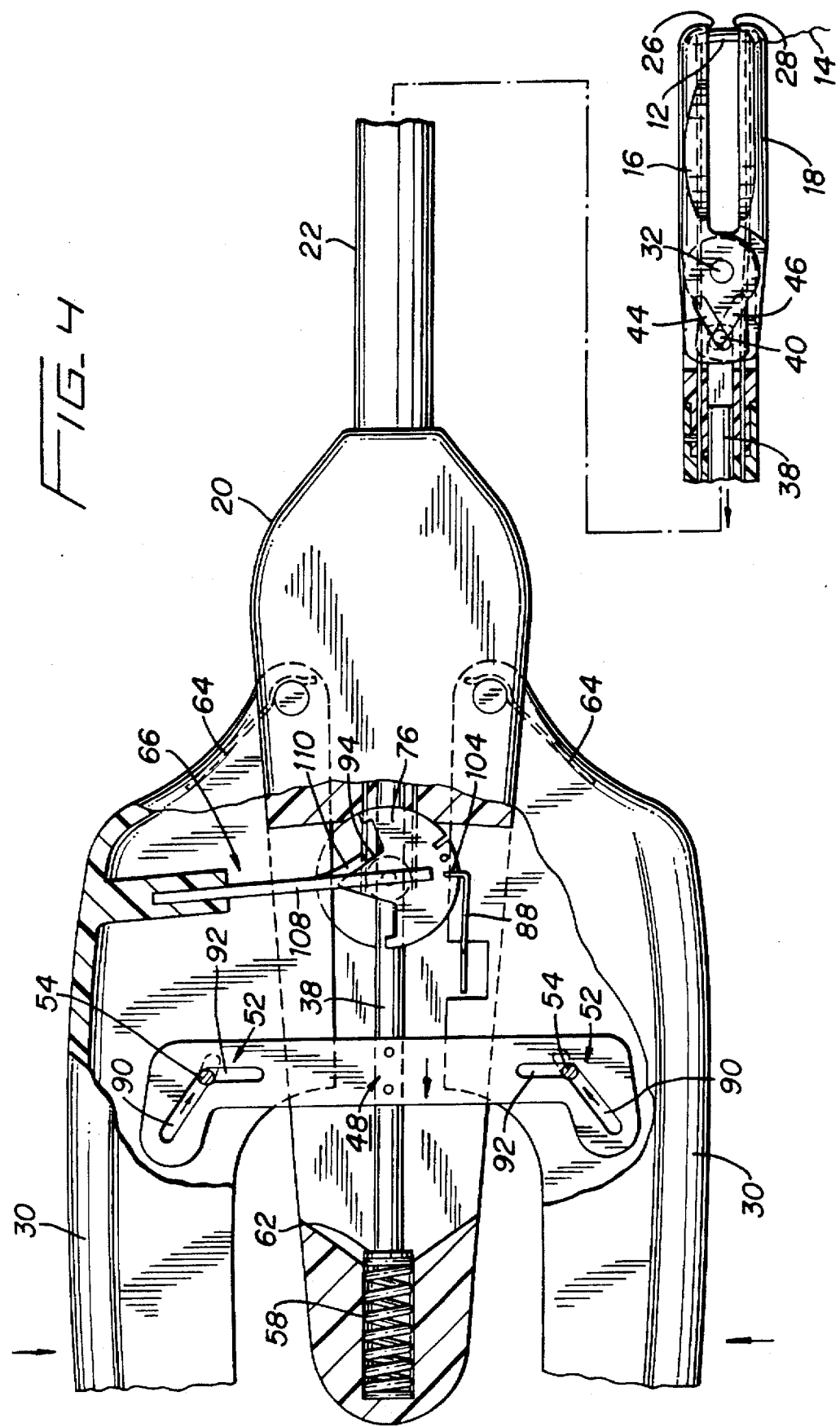

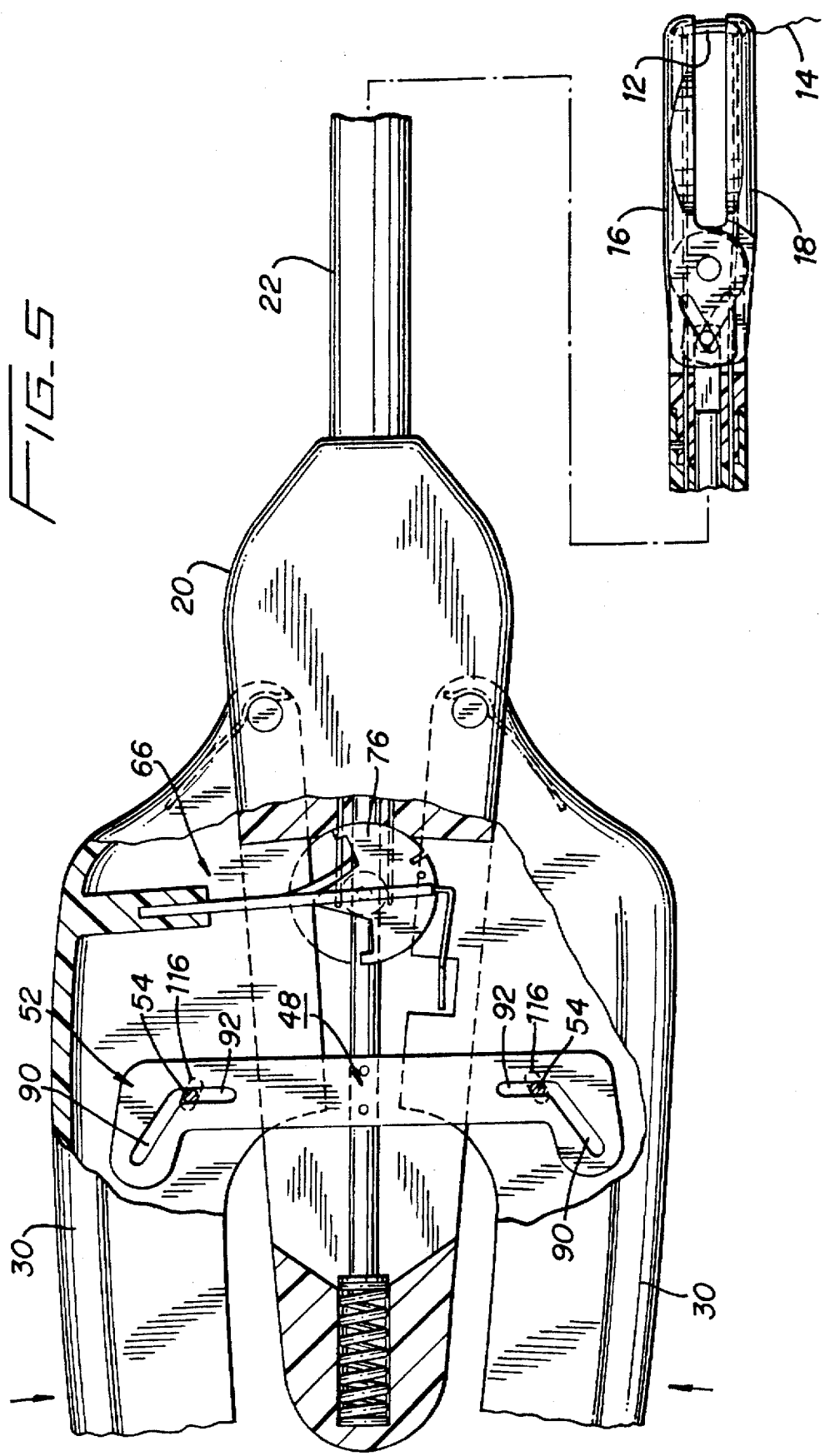

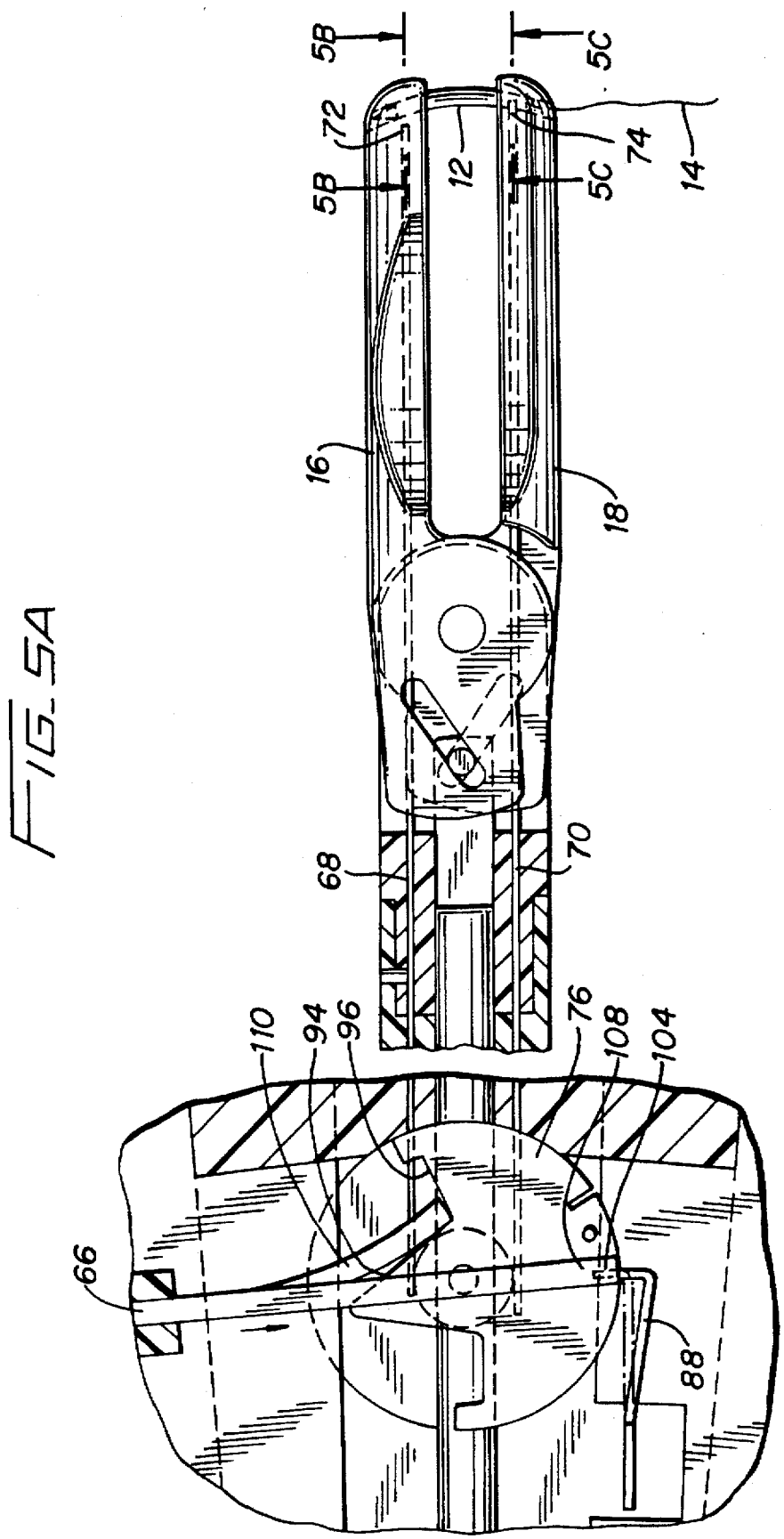

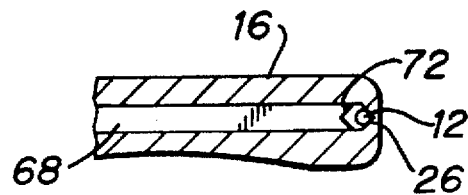
FIG._5B
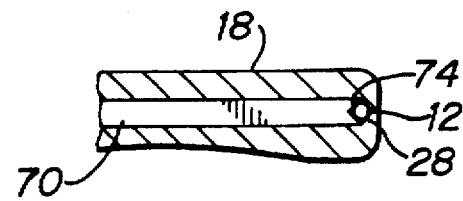
FIG._5C
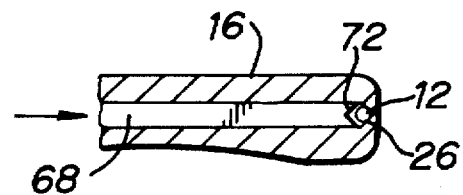
FIG._6B
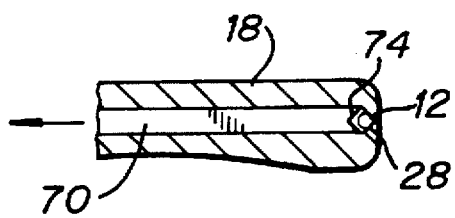
FIG._6C
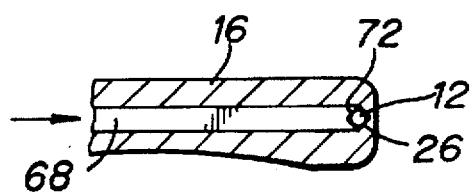
FIG._7A
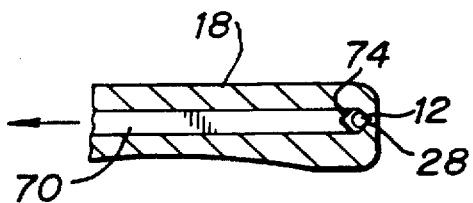
FIG._7B

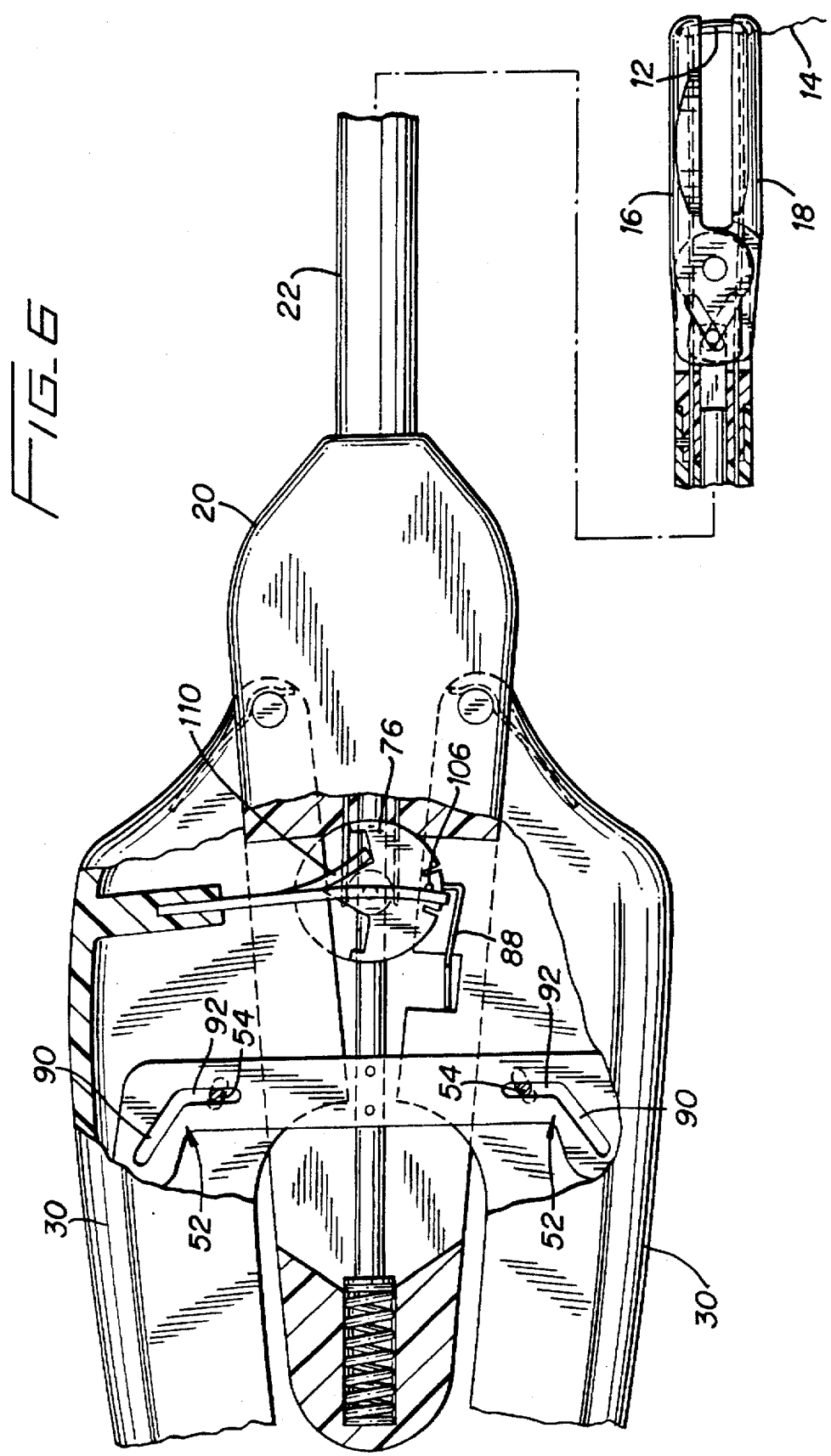

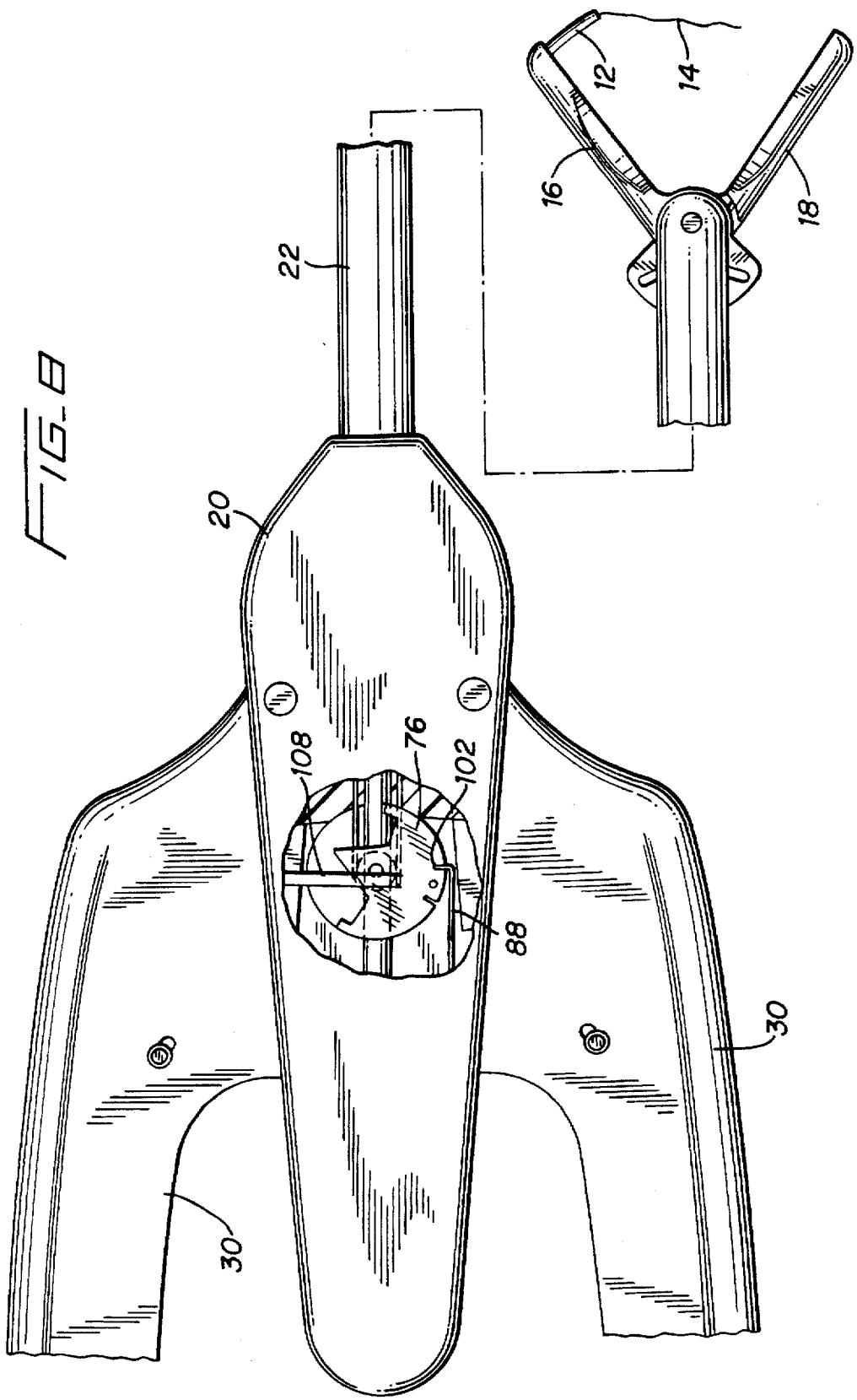

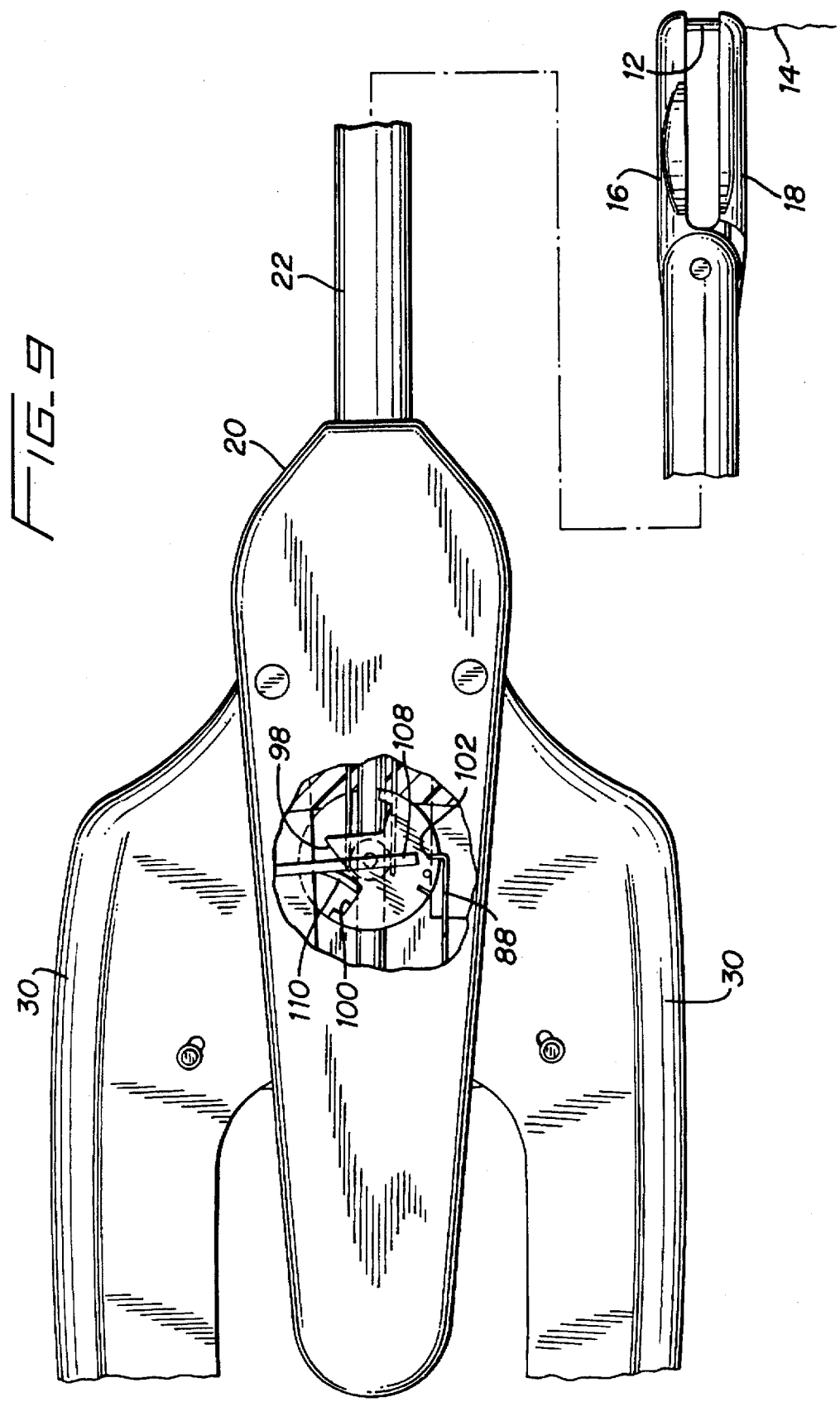

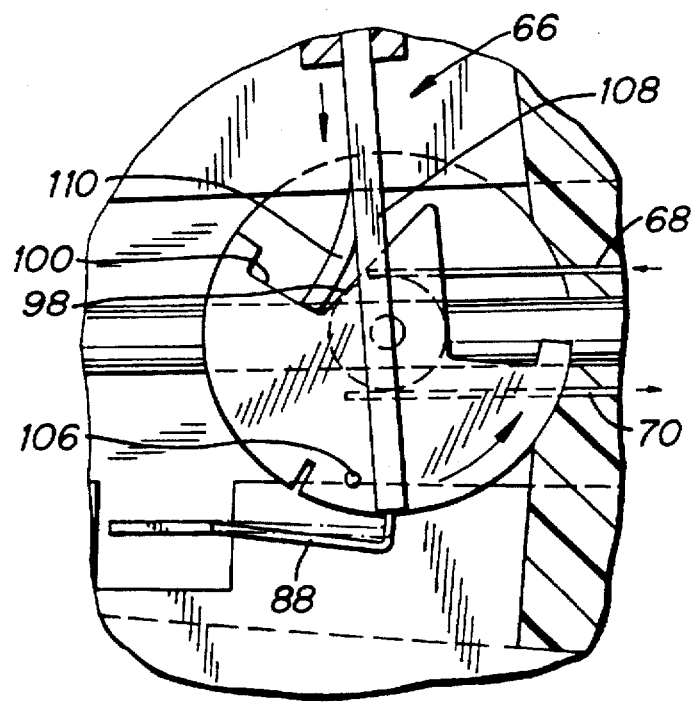
FIG_10
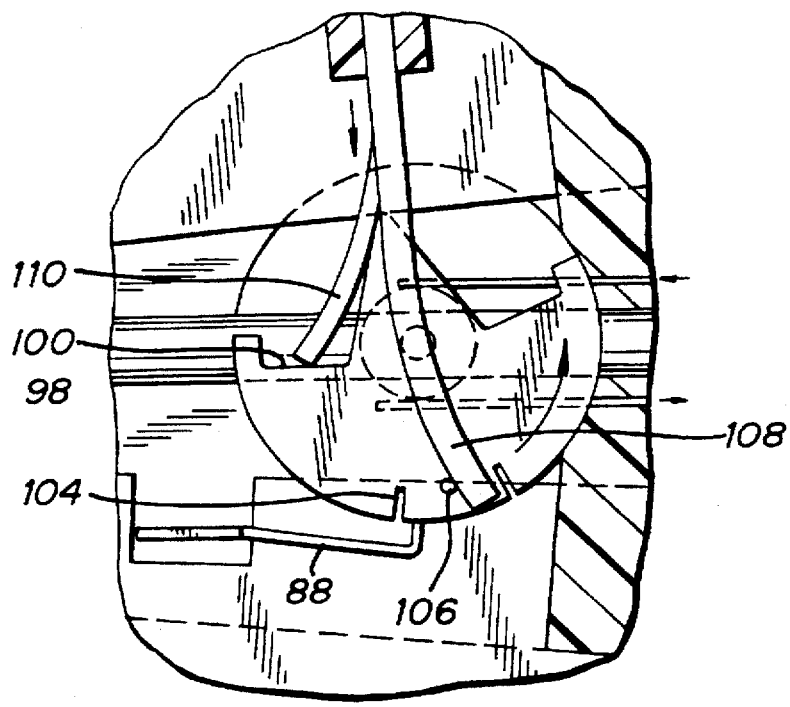
FIG_11

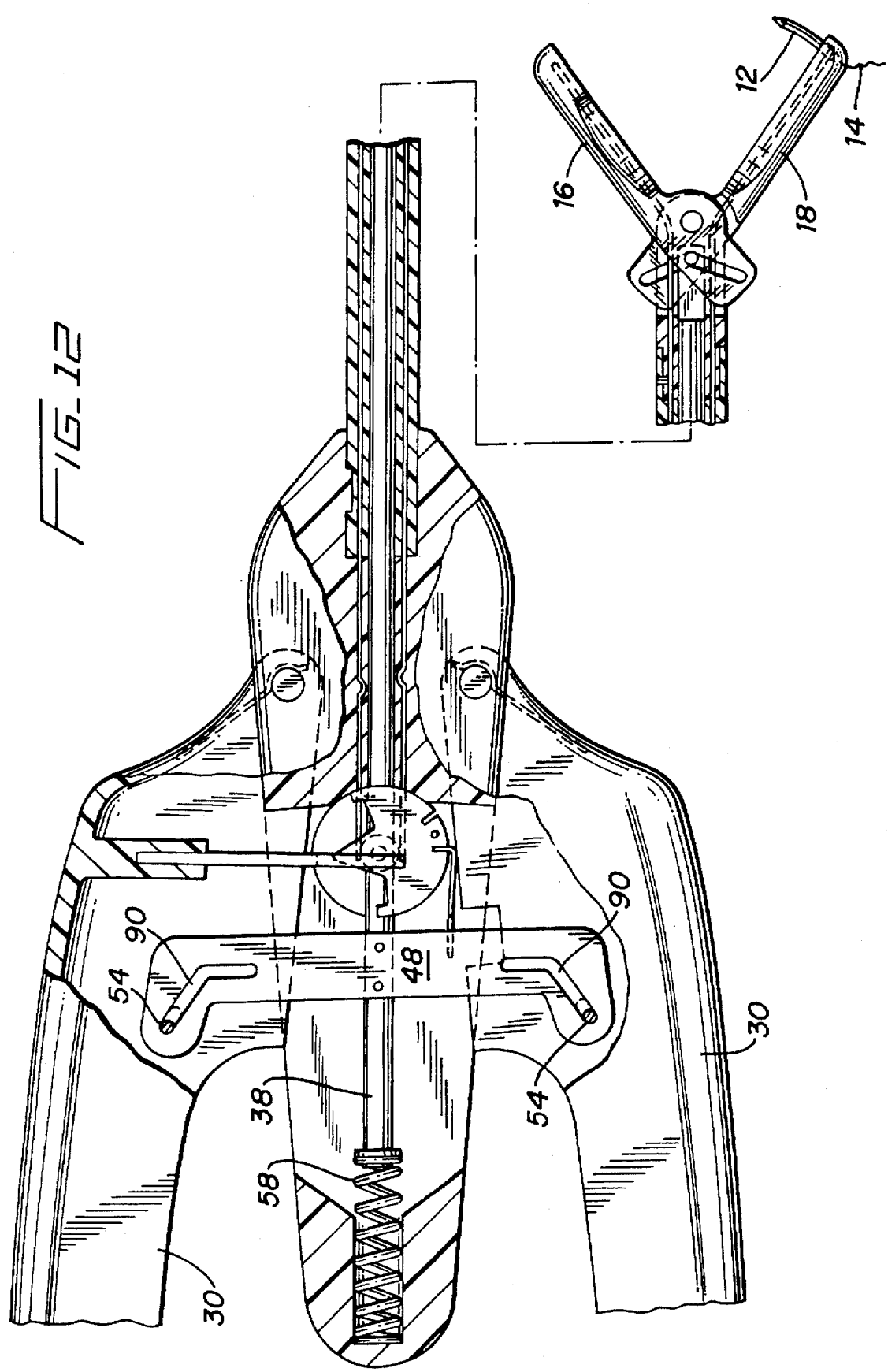

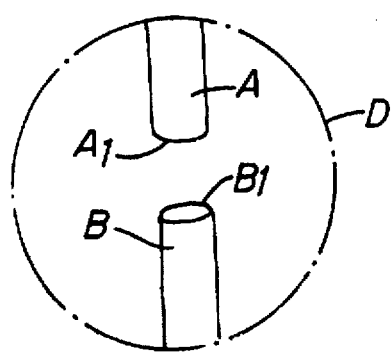
FIG._13A
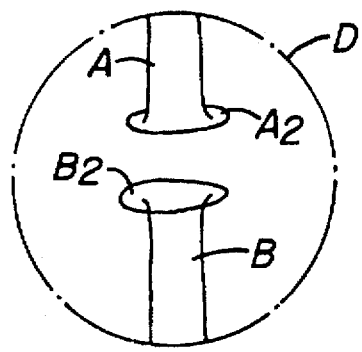
FIG._13B
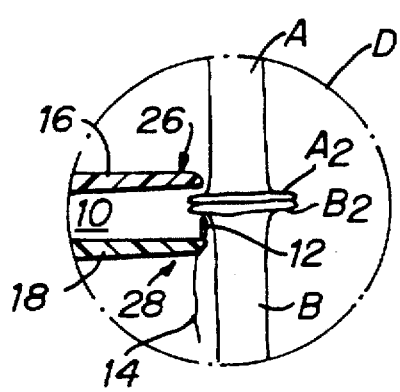
FIG._13C
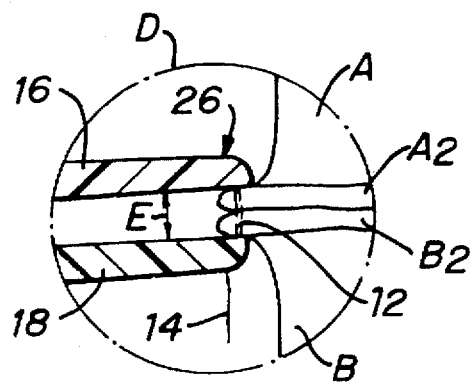
FIG._13D
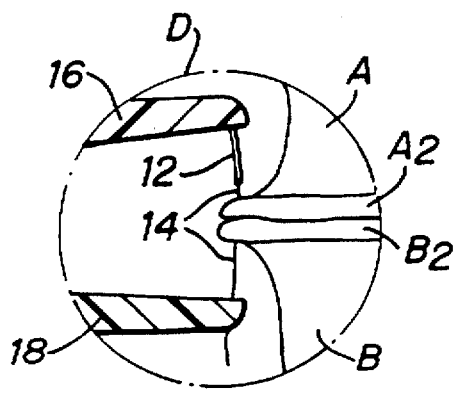
FIG._13E
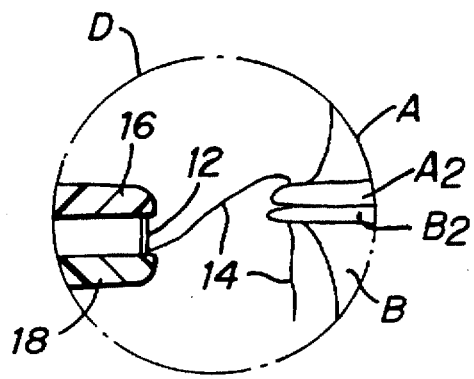
FIG._13F

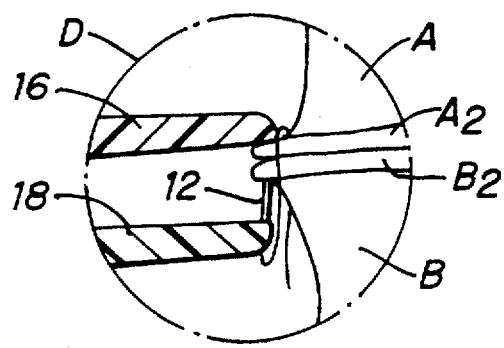
FIG._13G
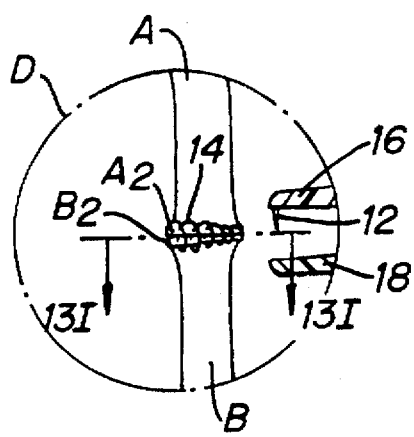
FIG._13H
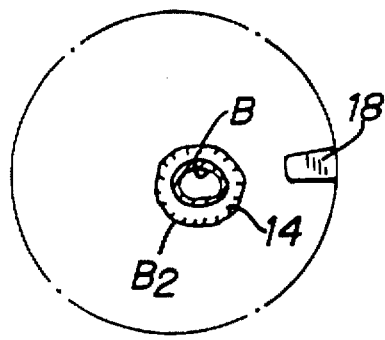
FIG._13I
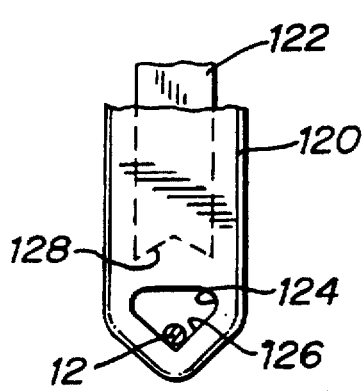
FIG._14A
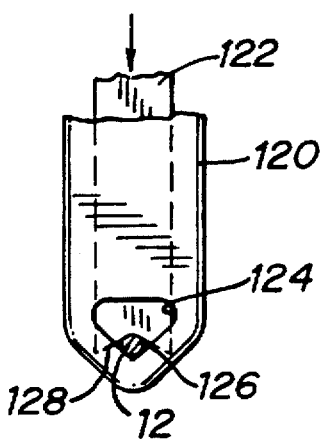
FIG._14B

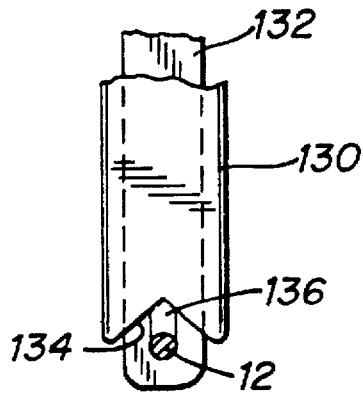
FIG_15A
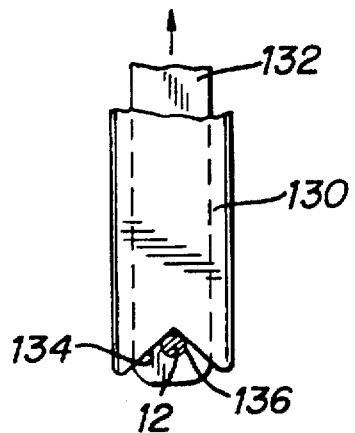
FIG_15B
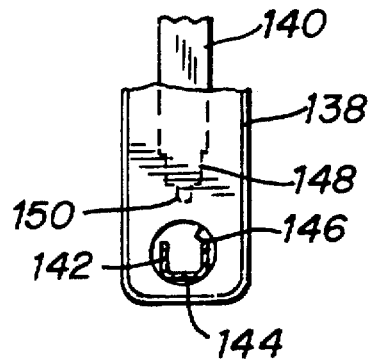
FIG_16A
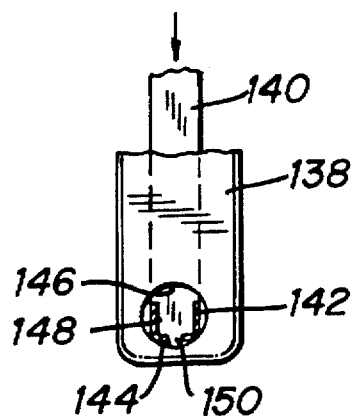
FIG_16B
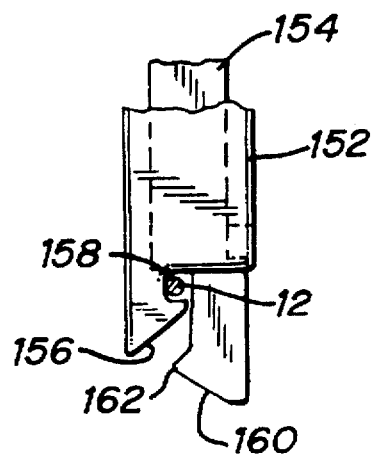
FIG_17A
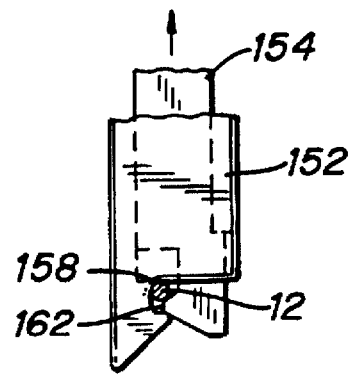
FIG_17B

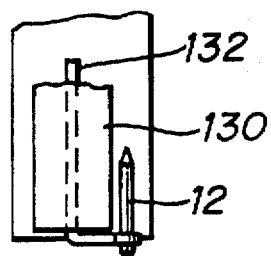
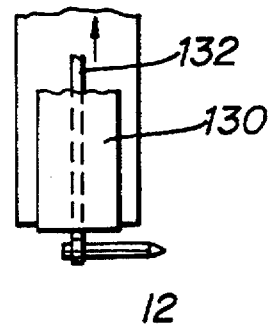
FIG_15C    FIG_15D
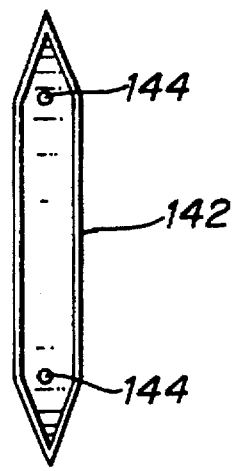
FIG_16C ized by the use of an elongated cannula structure having a relatively small diameter with a proximal and distal end. Laparoscopic and endoscopic suturing present a particularly challenging task, because they must be accomplished

ENDOSCOPIC VASCULAR SUTURING APPARATUS

CROSS REFERENCE TO RELATED APPLICATION

This application is a continuation of U.S. patent Ser. No. 08/319,840, filed Oct. 7, 1994 now abandoned.

BACKGROUND

1. Technical Field

The technical field relates generally to surgical suturing instrumentation and, more particularly, to a vascular surgical suturing apparatus suitable for use in endoscopic procedures and to a method for endoscopically suturing vascular tissue sections together.

2. Description of Related Art

During many surgical procedures it is often necessary to join or even rejoin portions of vascular tissues or vessels to form an anastomosis. Various methods of joining vascular tissues to create an anastomosis are used, such as, for example, suturing, stapling or clipping the ends of the vessels together. Additionally, various stents may be used to join the vessels together and create the anastomosis. Where vessels are joined open end to open end it is termed an "end to end" anastomosis. However, in certain surgical procedures it is often desirable to join a free open end of one vessel to an incision in the side of another vessel to create an "end to side" anastomosis or even an incision in the side of one vessel to an incision in the side of another vessel to form "side-to-side" anastomosis.

In some instances suturing of vessels is preferred over stapling or clipping the vessels. Due to the small size of the vessels, a very small suturing needle is used having a length of suture material attached thereto to suture the vessels together. The suturing needle is typically grasped by a needle holder and passed through one vessel and then the opposite vessel. The procedure is repeated to thread or impart a series of stitches to the vessels to suture them together.

Because of the extremely small size of the suturing needle used, typically on the order of ten thousands of an inch in diameter, handling problems may arise while manipulating the suturing needle through the vascular tissues. For example, upon piercing a vessel, the needle must be pushed through the vessel, released by the needle holder at one end of the needle and subsequently grasped at the opposite end of the needle to draw the needle and suture through the vessel thus requiring the release of the needle and suture during the procedure. Release of the needle is often undesirable and may pose problems in regaining control of the needle. To avoid this, it may become necessary to use two needle holders, one positioned on either side of the vessel, to continually grasp the needle, thereby requiring two hands to perform the operation. Additionally, precise control of the needle is often difficult when using typical needle holders. The small size of the needle also makes it difficult to recover if dropped during the surgical procedures, especially during endoscopic procedures if it is dropped in the body cavity.

These problems become magnified when the surgical procedures are carried out endoscopically or laparoscopically. Endoscopic or laparoscopic procedures are characterized by the use of an elongated cannula structure having a relatively small diameter with a proximal and distal end. Laparoscopic and endoscopic suturing present a particularly challenging task, because they must be accomplished through a port that typically averages between five and ten millimeters. Typically, the distal end of the cannula is passed through the surrounding tissue into the body cavity wherein the surgical procedure or examination is to be effected, thus providing a conduit for the insertion of surgical instrumentation. A plurality of cannula structures may be used to allow operation of a variety of instruments simultaneously during a given procedure. For example, one cannula may provide a conduit for an endoscope for vision and illumination within the operative cavity while the other cannulas may provide conduits for control of specialized surgical instruments designed for performing specific procedural functions.

While providing illumination and vision, endoscopes typically have a restricted or reduced filed of view. Thus, during a suturing operation, as the needle and suture material are passed through the vessels and pulled to draw the suture material through, it often becomes necessary to move the needle holder suturing apparatus from the field of view and may present problems in repositioning the needle within the restricted field of view to form another stitch in the vascular tissues. This increases the time required to suture the vessels together. Additionally, there is a limited space for maneuverability inside the body cavity and limited access to the body tissue, thus making endoscopic suturing quite difficult. The aforementioned minute size of the vessels and vascular surgical needles also add to the difficulty of endoscopic vascular suturing.

Thus, it would be advantageous to have a vascular surgical suturing apparatus and a method of suturing vessels which are particularly suited to suturing vascular tissues endoscopically or laparoscopically. It would also be advantageous to have a vascular surgical suturing apparatus which is capable of maintaining precise and constant control of the needle as it is passed from one needle holding jaw of the apparatus to another to avoid release of the needle during the suturing operation. It would be further advantageous to have a vascular surgical suturing apparatus which is capable of suturing vascular tissue sections together with limited apparatus and needle movement in order to maintain the entire suturing operation within a restricted field of view.

SUMMARY

There is disclosed an endoscopic surgical suturing apparatus which is particularly suited to suturing vascular tissue sections in endoscopic or laparoscopic procedures. The apparatus generally includes a handle housing an elongated tubular body portion extended distally therefrom. A pair of needle receiving jaws are pivotally mounted at a distal end of the body portion and are configured to repeatedly pass a surgical needle and associated length of suture material therebetween. A pair of handle members are provided to open and close the jaw members. The apparatus further includes needle holding structure in the form of a pair of needle engaging members which are mounted within the jaws for reciprocal movement into and out of needle holding recesses formed in the jaws. A reciprocating mechanism is provided to alternately advance and retract the needle engaging members.

Preferably, the reciprocating mechanism consists of a toggle wheel pivotally mounted within the handle housing and having first and second camming surfaces thereon. A camming lever is affixed to one of the handles and is engagable with the camming surfaces. The apparatus further includes a plate mounted within the handle housing and engagable with the handles such that initial closure of the handles closes the jaw members and continued closure of the handles rotates the toggle wheel to reciprocate the needle engaging members. There is also provided a lock member for preventing the toggle wheel from being rotated until the handle members have moved a predetermined distance and have fully closed the jaws.

There is also disclosed a method of suturing vascular tissue sections endoscopically including providing first and second needle receiving jaws which are mounted on an endoscopic portion and which are moveable with respect to each other and positioning a surgical needle having an associated length of suture material within one of the jaws and closing the jaws about a vascular tissue section causing the surgical needle pierce the tissue section. The method further includes the steps of releasing the surgical needle from the first jaw and grasping the needle within the second jaw when both jaws are in a closed position. The method additionally includes the step of opening the jaws to draw the length of suture material through the vascular tissue section.

BRIEF DESCRIPTION OF THE DRAWINGS

Various embodiments are described herein with reference to the drawings, wherein:

FIG. 1 is a perspective view of an endoscopic vascular surgical suturing apparatus with jaws in an open position and holding a surgical suturing needle within one of the jaws;

FIG. 2 is a perspective view of the apparatus of FIG. 1, with parts separated.

FIG. 3 is a side cross-sectional view of the suturing apparatus taken along line 3—3 depicted in FIG. 1;

FIG. 4 is a side cross-sectional view similar to FIG. 3 depicting the jaws moved to a closed position;

FIG. 5 is a side view of the vascular surgical suturing apparatus of FIG. 1, partially shown in section, illustrating initial actuation of the reciprocating mechanism;

FIG. 5A is an enlarged side view, partially shown in section, of the reciprocating mechanism position and the distal end of the suturing apparatus corresponding to the position of FIG. 5;

FIG. 5B is a cross-sectional view taken along the line 5B—5B of FIG. 5A;

FIG. 5C is a cross-sectional view taken along the line 5C—5C of FIG. 5A;

FIG. 6 is a view similar to FIG. 5, illustrating further actuation of the reciprocating mechanism;

FIG. 6B is a cross-sectional view taken along the lines 6B—6B of FIG. 6A;

FIG. 6C is a cross-sectional view taken along the lines 6C—6C of FIG. 6A;

FIG. 7A is cross-sectional view taken along the line 7A—7A of FIG. 7;

FIG. 7B is cross-sectional view taken along the line 7B—7B of FIG. 7;

FIG. 8 is a side view of the vascular surgical suturing apparatus, partially shown in section, with the jaws in the open position and illustrating the surgical needle having been passed to the opposing jaw;

FIG. 9 is a view similar to FIG. 8 with the jaws moved to the closed position;

FIG. 10 is an enlarged side view, particularly shown in section, of the reciprocating mechanism illustrating initial actuation of the reciprocating mechanism in an opposite (counterclockwise) direction;

FIG. 11 is an enlarged side view similar to FIG. 10, illustrating further actuation of the reciprocating mechanism;

FIG. 12 is a side view, similar to FIG. 3, illustrating the needle passed back to an initial jaw;

FIG. 13A is a perspective view of a pair of vascular tissue sections to be sutured as viewed within a limited field of view endoscopically;

FIG. 13B is a view similar to FIG. 13A with the ends of the vessels everted in preparation for suturing;

FIG. 13C is a sectional view of a distal end of the surgical suturing apparatus of FIG. 1 and the pair of everted vessels ready for suturing;

FIG. 13D is a view similar to FIG. 13C illustrating the piercing of the everted edges of the vascular sections by the suturing needle;

FIG. 13E is a view similar to FIG. 13D illustrating the suture needle having been passed to an opposing jaw and the suture being drawn through the everted vessel edges;

FIG. 13F is a view similar to view 13E illustrating the surgical needle being passed back to the first jaw.

FIG. 13G is a view similar to FIG. 13D illustrating the jaws being closed again about the everted vessel ends to pierce the vessels and form another stitch;

FIG. 13H is a view of the vessels sutured together to form an anastomosis;

FIG. 13I is a view taken along the line 13I—13I of FIG. 13H;

FIGS. 14A and 14B are enlarged views of an alternate suturing apparatus jaw distal end and associated needle engaging member configuration;

FIGS. 15A–15D are enlarged views of an another alternate jaw distal end and needle engaging member configuration;

FIGS. 16A and 16B are enlarged views of a further alternate distal end and needle engaging member configuration for use with a suturing needle having a hole at least partially therethrough;

FIG. 16C is a side plan view of a double pointed suturing needle having a hole at least partially therethrough;

FIGS. 17A and 17B are enlarged views of another alternate distal end and needle engaging member arrangement;

DESCRIPTION OF PREFERRED EMBODIMENTS

Figure 1A:
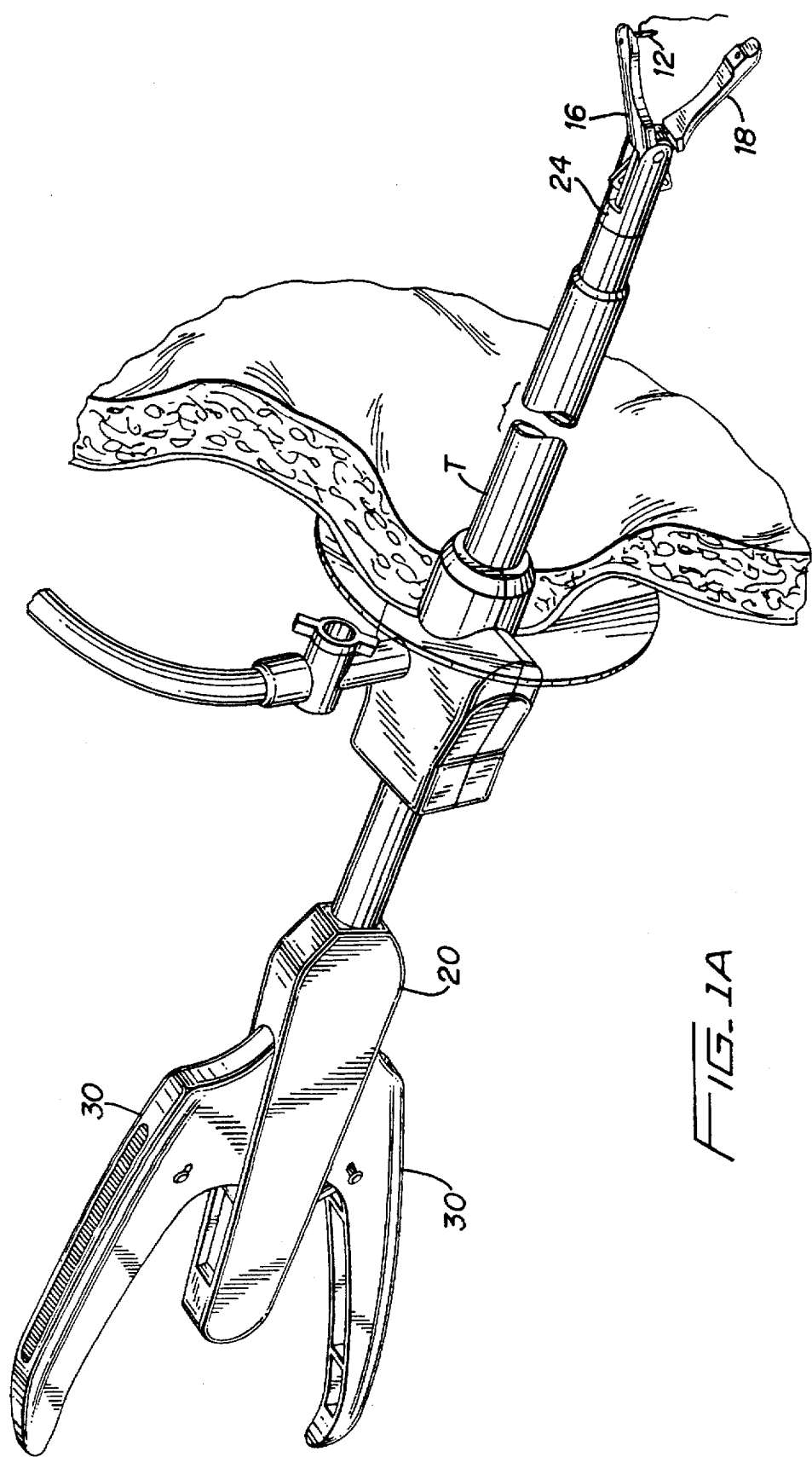
FIG. 1A is a perspective view of the endoscopic vascular surgical suturing apparatus inserted through a trocar cannula.

Referring to FIG. 1, there is depicted an endoscopic vascular suturing apparatus 10 which is particularly suited to facilitate suturing vascular tissue sections or vessels together when viewed within a restricted field of view during endoscopic or laparoscopic procedures. Further, apparatus 10 is specifically designed to repeatedly pass a small scale surgical needle, having an associated length of suture material attached thereto, such as, for example, surgical needle 12 and suture 14, through vascular tissue sections while maintaining precise control of needle 12 during all phases of the suturing operation. Apparatus 10 is designed to pass suturing needle 12 and suture 14 repeatedly between a pair of jaws 16 and 18.

Apparatus 10 is preferably designed to handle surgical needles 12 having a length of approximately 0.1 to 0.5 inches and a diameter of approximately ten thousandths to 0.025 of an inch. Preferably, surgical needle 12 has a diameter substantially equal to that of the affixed suture to prevent fluids from leaking from the vessel between the needle hole and suture during suturing.

Surgical suturing apparatus 10 generally includes a handle portion 20, and an elongated tubular housing or body portion 22 extending distally from the handle portion 20. Body portion 22 is preferably dimensioned to be insertable into a tubular cannula having an internal diameter on the order of five millimeters to twelve millimeters for endoscopic/laparoscopic procedures. Needle receiving jaws 16 and 18 are pivotally mounted with respect to body portion 22 for movement by handle members 30 between an open position spaced apart from each other and a closed position wherein jaws 16 and 18 are in close cooperative alignment for grasping the vascular tissue sections to be sutured and passing surgical needle 12 between them. Preferably jaws 16 and 18 have atraumatic tissue engaging surfaces 17 and 19, respectively, which may be ridged along theft entire length or only a portion thereof. Jaws 16 and 18 are preferably mounted for pivotal movement on a jaw support member 24 which is affixed to a distal end of body portion 22. Jaws 16 and 18 include needle receiving recess 26 and 28, respectively, which are configured to surround and hold at least a portion of the surgical needle 12 disposed therein substantially perpendicular to tissue engaging surfaces 17 and 19. Needle receiving recesses 26 and 28 may have various cross sectional shapes, such as, for example, square, rectangular, diamond shaped, etc., and preferably are of circular cross-section.

Referring now to FIG. 2, jaws 16 and 18 are pivotally mounted on support member 24 by means of a jaw pivot pin 32 which extends through holes 34 in support member 24 and pivot holes 36 in each of jaw members 16 and 18. To move jaws 16 and 18 between an open position and a closed position there is provided an axially or longitudinally moveable center red 38 having a camming pin 40 mounted at a distal end 42 thereof. Camming pin 40 rides in and engages angled camming slots 44 and 46 in jaws 16 and 18, respectively, such that distal movement of center rod 38 causes jaws 16 and 18 to be cammed into an open position and proximal movement of center rod 38 causes jaws 16 and 18 to be cammed into the closed position. As defined herein, "distal" refers to the portion of apparatus 10 closer to the jaws, while "proximal" refers to the portion of the instrument closer to the handle.

Handle members 30 are connected to center rod 38 by a plate 48 which is affixed to a proximal end 50 of center red 38. Plate 48 includes a pair of camming slots 52 and is connected to handle members 30 by pins 54 which ride in slots 52. Handles 30 are pivotally connected to housing 20 by pivot pins 56. Thus, closing handles 30 toward handle portion 20 drives plate 48, and thus center rod 38, proximally thereby camming jaws 16 and 18 to a closed position, while opening handles 30 drives plate 48 distally to cause jaws 16 and 18 to be cammed into the open position.

During certain surgical operations it is preferable that the jaws of suturing apparatus 10 be biased to an open position thereby requiring the operator to squeeze handles 30 together to move jaws 16 and 18 to a closed position. Thus, there is provided a jaw biasing spring 58 which resides in a channel 60 formed within housing 20. Spring 58 abuts a spring washer 62 affixed to proximal end 50 of center rod 38 and biases center rod 38 distally. The biasing action of spring 58 also aids in pulling suture 14 through the tissue sections upon opening of arms 16 and 18. In many instances, certain further ergonomic and operational advantages may be obtained by biasing handle member 30 in an initially open position. Thus, in this embodiment, there are provided a pair of leaf springs 64 which are affixed to pivot pins 56.

Handle members 30 initially close jaws 16 and 18 and subsequently automatically pass the surgical needle 12 between the jaws. More specifically, as shown in FIGS. 3 and 4, pins 54 slide distally in angled jaw closing segment 90 of slots 52 in plate 48 to close the jaws. Once the jaws are closed, continued depression of handle members 30 results in pins 54 entering in perpendicular transfer segments 92 of slots 52. (FIG.5). Transfer segments 92 are oriented substantially perpendicular to center red 38 and thus allow the motion of center red 38 and consequently the movement of jaws 16, 18 to dwell or cease as handle members 30 continue to be compressed. However, during this continued compression, the mechanism for transferring the needle between the jaws is actuated. This is discussed in detail below. It will be noted that as handle members 30 are closed they move pins 54 through an arc having a radius defined by distance between pins 54 and handle pivot pins 56. Thus, to allow pins 54 to move within transfer segments 92, handle members 30 include a pair of compensating slots 116 which allow pins 54 to move slightly relative to handle members 30 such that pins 54 may move straight downwardly within transfer segments 92.

Alternatively, it is within the knowledge of those skilled in the art to form transfer segment 92 arcuately rather than perpendicular to center rod 38. Thus, by forming transfer segments 92 with an arc having a radius identical to that described by pin 54, there would be no need for compensating slots 116 in handle members 30. Additionally, various other structures may be provided to compensate for the arcuate motion of pins 54 during handle closure.

As noted hereinabove, apparatus 10 is particularly suited for suturing extremely small vessels or vascular tissue sections when viewed within the restricted field of view available during endoscopic procedures. Further, suturing of vessels requires an extremely small needle 12 and suture 14, typically on the order of then thousands of an inch in diameter. However, to prevent the vascular tissue sections from being compressed or crushed during the suturing operation, a working gap is maintained between jaws 16 and 18, respectively, such that they do not touch upon closure. However, jaws 16 and 18 do close sufficiently such that needle 12 may be precisely exchanged therebetween.

Although the preferred method of moving jaws 16 and 18 is by pivotal motion, parallel movement of jaws 16 and 18 is also contemplated. Parallel movement of jaws 16 and 18 is especially desirable when using relatively straight surgical needles and may be accomplished in several ways. For example, jaws 16 and 18 could be mounted with respect to each other to both move perpendicular to their respective longitudinal axes. Alternately, jaws 16 and 18 could be mounted to move or slide parallel to their respective longitudinal axes to advance and retract their distal ends. When jaws 16 and 18 slide relative to each other, it is preferable to have the distal faces of the jaws open to a needle holding recess to facilitate transfer of a surgical needle or surgical incision member therebetween. One embodiment of such parallel moving jaws is discussed below with respect to FIG. 22A. Moreover, to facilitate transfer of needle 12 between jaws 16 and 18, needle 12 preferably has a radius of curvature which is substantially equal to the distance between either of needle recesses 26, 28 and the jaw pivot point, i.e., jaw pivot pin 32, of apparatus 10. In this manner the radius of curvature of surgical needle 12 matches the arc defined by the recesses about the pivot point on closure of jaws 16 and 18. As noted above however, when apparatus 10 is formed with a parallel closing style arm structure it may be preferable to have a straight surgical needle.

With reference to FIGS. 2 and 3, apparatus 10 further includes holding structure to alternately secure needle 12 within jaw recesses 26 and 28 of jaws 16 and 18, respectively. The holding structure allows surgical needle 12 to be initially held within one of the jaws and, upon closure of the handles, to be subsequently passed to the opposite jaw. To facilitate single handed use of apparatus 10, a cam actuating lever 66 is provided to automatically actuate the holding structure upon full closure of the handles. Cam actuating lever 66 is affixed to one of the handle members 30. Upon closure of handle members 30, cam actuating lever 66 automatically actuates the holding mechanism and thereby transfers surgical needle 12 to an opposite jaw.

In order to hold or secure needle 12 within jaws 16 and 18, there are provided a pair of needle engaging members or blades 68, 70 which are longitudinally movable within longitudinally extending channels 112, 114 of body portion 22. First needle engaging member 68 is at least partially slidably disposed within first jaw 16 while a second needle engaging member 70 is at least partially slidably disposed within second jaw 18.

Distal ends 72 and 74 of needle engaging members 68 and 70 respectively, are provided with suitable engagement structure for engaging an edge of surgical needle 12 to securely hold needle 12 within recesses 26, 28 formed in first and second jaws 16 and 18. Thus, as shown in FIGS. 5B, 5C, distal ends 72 and 74 of needle engaging members 68 and 70 include V-shaped camming edges to cam or wedge surgical needle 12 within respective recesses 26 and 28. Upon engagement of surgical needle 12 with one of needle engaging members 68 or 70, it is securely held within the associated jaw 16 or 18. While the preferred needle engaging member engagement structure includes V-notches, it will be appreciated by those skilled in the art the various other configurations of needle engaging member distal ends 72 and 74 may be provided to securely hold needle 12 within jaws 16 and 18. Thus, alternate structure in either jaws 16 or 18 or alternate structure in needle 12 itself such as, for example, notches in an edge of needle 12, or holes completely therethrough, may be provided to accept corresponding engagement structure formed on needle engaging members 68 and 70. Thus, for example, a double-pointed surgical needle, or surgical incision member, having suture attachment structure intermediate the points may be utilized. One example of a surgical incision member is disclosed in U.S. Pat. No. 5,569,301, filed Jun. 16, 1994, and entitled SURGICAL INCISION MEMBER the disclosure of which is incorporated by reference herein. Several of these alternate structures are discussed in detail below.

As shown in FIG. 3, needle engaging members 68, 70 are slightly bowed at portions 68a, 70a respectively, thereby automatically adjusting to needles of various diameters. That is, as the needle is clamped, the needle engaging member buckles at a predetermined location so that the spring force applied to the needle is constant, regardless of the needle diameter. The needle engaging member is slightly buckled even when the needle is not clamped to ensure that the increased buckling occurs in the same area whenever the needle is clamped.

Referring now to FIGS. 2 and 3, to repeatedly pass needle 12 between jaws 16 and 18, a reciprocating mechanism in the form of a toggle wheel 76 is provided within handle portion 20 and is affixed by pins 84, 86 to proximal ends 78 and 80 of first and second needle engaging members 68 and 70, respectively. Toggle wheel 76 is rotatable about pivot pin 82 in the clockwise and counterclockwise direction. Toggle wheel 76 alternately advances and retracts needle engaging members 68 and 70 within jaws 16 and 18, respectively, thereby alternately moving needle engaging members 68 and 70 into engagement with needle 12. Thus, toggle wheel 76, along with first and second needle engaging members 68 and 70, provide the holding structure for securely and alternately holding and passing needle 12 within needle receiving recesses 26 and 28 formed in jaws 16 and 18.

Cam actuating lever 66 actuates toggle wheel 76 automatically upon closure of jaws 16 and 18. In order to prevent inadvertent release of surgical needle 12 from jaws 16 or 18 prior to closure of the jaws, there is provided a lock member 88 which is flexibly mounted within handle portion 20. Lock member 88 is engagable with toggle wheel 76 to prevent movement of toggle wheel 76, and thus release of needle 12, when jaws 16 and 18 are in a open position, i.e., when handle members 30, and thus cam actuating lever 66, have not been depressed. Slots 52 in plate 42 allow cam actuating lever 66 to engage toggle wheel 76 once jaws 16 and 18 have been moved to the closed position. As noted above, the transfer segment 92 dwells the movement of jaws 16 and 18 during the continued closure of handle members 30 and actuation of toggle wheel 76.

With continued reference to FIG. 3, toggle wheel 76 is provided with a first angled camming surface 94 having a first ledge 96 which, when engaged by cam actuating lever 66, translates to a clockwise rotation of toggle wheel 76 and thus a distal advancement of needle engaging member 68 and a proximal retraction of needle engaging member 70. Similarly, a second angled camming surface 98 and second ledge 100 are provided, such that when engaged by cam actuating lever 66, toggle wheel 76 is rotated in a counterclockwise direction to advance second needle engaging member 70 and retract first needle engaging member 68.

As noted hereinabove, toggle wheel 76 provides engagement structure for engagement with lock member 88. Preferably, toggle wheel 76 is provided with lock notches 102 and 104 which correspond to the distalmost advancement of first and second needle engaging members 68 and 70, respectively. Thus, when toggle wheel 76 is rotated counterclockwise to a position where lock member 88 engages lock notch 104, second needle engaging member 70 is locked into an advanced or distalmost position to securely hold needle 12 within jaw 18. Likewise, when toggle wheel 76 is rotated clockwise to a position where lock member 88 engages lock notch 102, first needle engaging member 68 is locked into an advanced or distalmost position locking needle 12 within jaw 16. Thus, lock member 88, in conjunction with lock notches 102 and 104, prevents release and transfer of needle 12 when jaws 16 and 18 are not fully closed. Cam actuating lever 66 is provided to automatically perform the dual sequential functions of unlocking toggle wheel 76 from engagement with lock member 88 and rotating toggle wheel 76. Cam actuating lever 66 includes a flexible release leg 108 which is provided to cam lock member 88 out of lock notches 102 or 104 and thus allow toggle wheel 76 to be rotated. Cam actuating lever 66 also includes a flexible toggle leg 110 formed parallel to release leg 108. Toggle leg 110 is engagable with angled first and second camming surfaces 94 and 98 and first and second ledges 96 and 100 in order to rotate toggle wheel 76 upon closure of jaws 16 and 18.

Figure 6A:
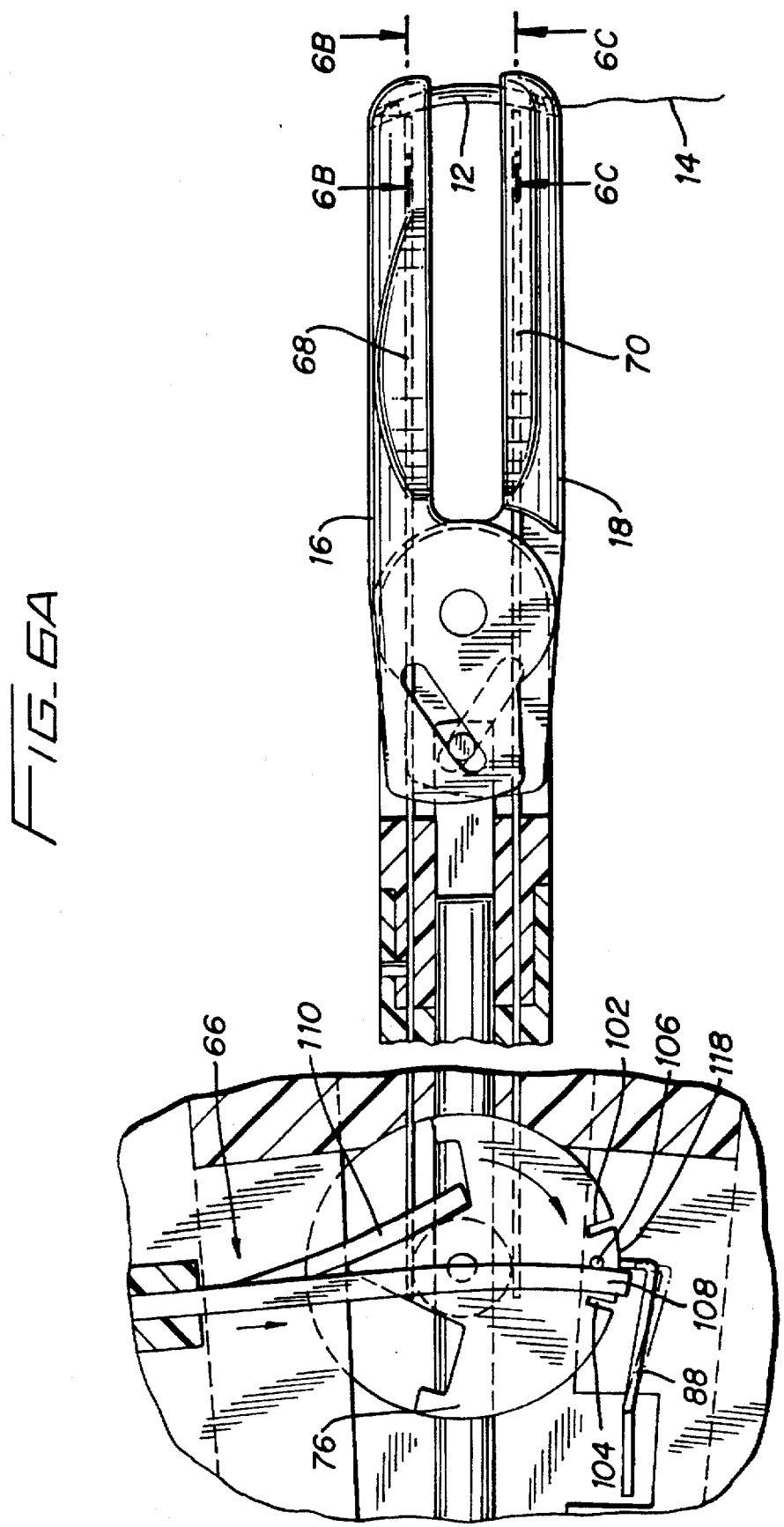
FIG. 6A is an enlarged side view, partially shown in section, of the reciprocating mechanism position and distal end of the suturing apparatus corresponding to the position of FIG. 6.
Figure 7:
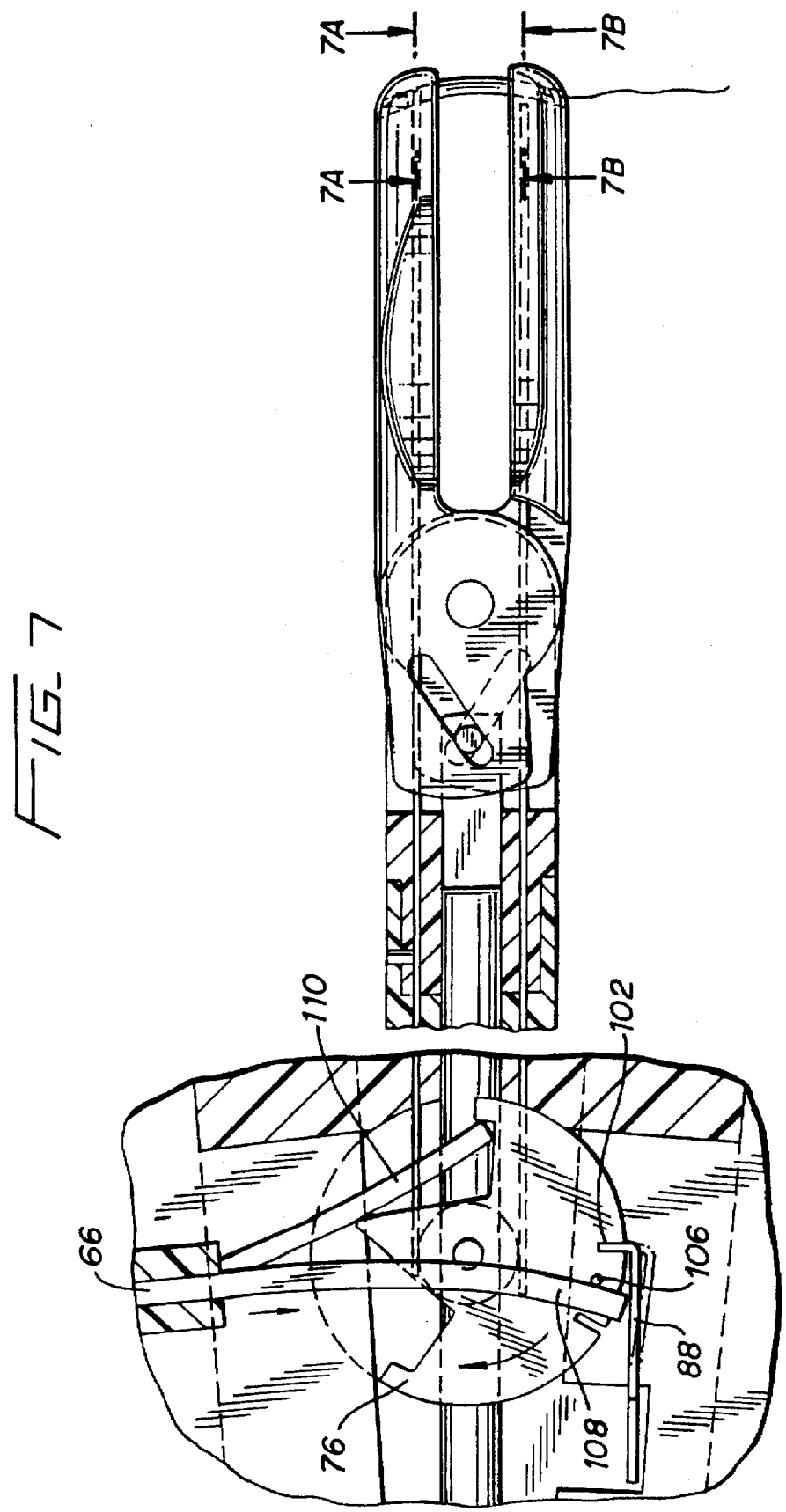
FIG. 7 is a view similar to FIG. 6A, illustrating a final position of the reciprocating mechanism.

Toggle wheel 76 is also provided with a knock off pin 106 to aid lock member 88 in entering lock notches 102 and 104. More specifically, knock off pin 106 functions to move flexible release leg 108 away from locking member 88 (FIG. 6A). That is, when handle members 30 are depressed, it causes release leg 108 to move lock member 88 out of lock notch 104, and lock member 88 is held down and away from toggle wheel 76 by release leg 108. Thus, to allow lock member 88 to spring back up and into engagement with lock notch 102 upon complete rotation of toggle wheel 76, knock off pin 106 is provided to move flexible release leg 108 away from lock member 88. Thus, as shown, when toggle wheel 76 is rotated in a clockwise direction, knock off pin 106 moves into abutment with a lower end of release leg 108.

Referring now to FIGS. 1–11, and initially to FIG. 1, the operation of endoscopic vascular suturing apparatus 10 will now be described. As noted hereinabove, apparatus 10 is particularly suited to repeatedly pass surgical needle 12 back and forth between jaws 16, 18 automatically upon full closure of the handles.

In the initial position, jaws 16 and 18 are biased to an open position by spring 58. Needle 12, having an associated length of suture material 14 attached thereto, is positioned and held within recess 28 of second jaw 18. Referring now to FIG. 3, handle members 30 are in an open state holding cam actuating lever 66 away from toggle wheel 76 in the initial position.

In this initial position, toggle wheel 76 is in a counterclockwise most position with lock member 88 engaging and securing toggle wheel 66 by engagement with lock notch 104. Thus, surgical needle 12 is locked into second jaw 18.

Referring now to FIG. 4, to actuate vascular suturing apparatus 10, handle members 30 are pivoted inwardly towards handle portion 20. As handle members 30 are pivoted, pins 54 are driven within jaw closing segments 90 of slots 52. As pins 54 move within jaw closing segments 90, plate 48 is forced in a proximal direction. Proximal movement of plate 48 pulls center red 38 proximally thereby compressing spring 58. As center rod 38 is moved proximally, center rod camming pin 40 moves proximally within first and second jaw camming slots 44 and 46 respectively, to thereby pivot jaws 16 and 18 closed about pivot pin 32. As jaws 16 and 18 are pivoted closed, needle 12 enters recess 26 in jaw 16.

As shown, upon pivoting handle members 30, cam actuating lever 66 is moved towards toggle wheel 76. Thus toggle leg 110 is forced against first angled camming surface 94. However, since lock member 88 is still engaged in first lock notch 104, toggle wheel 76 does not reciprocate. Thus apparatus 10 has been manipulated to close jaws 16 and 18 about surgical needle 12 without initiating reciprocation of needle engaging members 68 and 70. Handle members 30 are partially closed against the bias of leaf springs 64 which now assume a stressed state. As shown, upon closure of handle members 30, cam actuating lever 66 and, thus release leg 108, is rotated into alignment above lock member 88.

Referring to FIGS. 5B and 5C, when toggle wheel 76 is in a counter clockwise most position with lock member 88 engaging lock notch 104, second needle engaging member 70 is in a distally advanced position causing distal end 74 of needle engaging member 70 to engage an edge of surgical needle 12. First needle engaging member 68 is in a proximalmost position with its distal end 72 disassociated from surgical needle 12.

As noted above, transfer segments 92 of slots 52 in plate 48 provide a dwell period during which handle members 30 may be closed to bring cam actuating member 66 into engagement with toggle wheel 76 without causing any further pivotal movement of jaws 16 and 18. Thus, as shown in FIG. 5A, as cam actuating lever 66 is moved downwardly, release leg 108 contacts lock member 88 and moves lock member 88 out of engagement with lock notch 104. Thus, toggle wheel 76 is released for rotation. As noted hereinabove, cam actuating lever 66 forms the dual sequential functions of disengaging lock member 88 from toggle wheel 76 and rotating toggle wheel 76. Thus, after lock member 88 has been disengaged from lock notch 104, toggle leg 110 contacts first angled camming surface 94 and first ledge 96 to initiate rotation of toggle wheel 76 in a clockwise direction.

Referring now to FIG. 6, further pressure on handle members 30 drives pins 54 further within transfer segments 94 and causes toggle leg 110 to initiate rotation of toggle wheel 76 in a clockwise direction. Clockwise rotation of toggle wheel 76 begins to advance first needle engaging member 68 in a distalmost direction and retract second needle engaging member 70 in a proximalmost direction.

As toggle leg 110 rotates toggle wheel 76 in a clockwise direction, knock off pin 106 moves release leg 108 away from and off of lock member 88. Thus, as toggle wheel 76 is rotated, lock member 88 now rides along, and is held down by, a lower circumferential surface 118 of toggle wheel 76. Needle engaging members 68 and 70 continue to be advanced and retracted respectively. As noted above, when jaws 16 and 18 are in a closed position, surgical needle 12 is held or contained within recesses 26 and 28. Thus upon rotation of toggle wheel 76, to cause needle engaging member 68 to advance and needle engaging member 70 to retract, surgical needle 12 is seemly contained within closed jaws 16 and 18 when neither needle engaging member 68 and 70 are in engagement with surgical needle 12. This non-engagement of the needle engaging members 68, 70 is illustrated in FIGS. 6B, 6C as the V-shaped camming edges 72, 74, respectively, are out of contact with the surgical needle 12.

Further movement of cam actuating lever 66 (FIG. 7), due to depression of handle member 30, results in toggle leg 110 rotating toggle wheel 76 to a fully clockwise or final position. Release leg 108 is held out of alignment with lock member 88 by knock off pin 106. Thus, as toggle wheel 76 is rotated to the final position, lock notch 102 assumes a position directly above lock member 88 and lock member 88, being spring biased, moves upward to engage lock notch 102. Thus, toggle wheel 76 again becomes blocked or locked out from further rotation. Any further depression of handle members will cause no further rotation of toggle wheel 76.

V-shaped camming edge in needle engaging member 68 has now been advanced into engagement and securely lock surgical needle 12 within jaw 16 while V-shaped camming edge in needle engaging member 70 has been moved to a proximalmost position disassociated from surgical needle 12 (see FIGS. 7A, 7B). Thus, in this manner, control of surgical needle 12 has been transferred from jaw 18 to jaw 16 while containing needle 12 within recesses 26 and 28, thereby accomplishing the transfer of needle 12 from jaws 18 to 16 without risk of release or escape of needle 12 from apparatus 10.

As shown in FIG. 8, to complete the operation of vascular suturing apparatus 12, as pressure is released from handle members 30, springs 64 (FIG. 3) bias handle members 30, and thus jaws 16 and 18, into an open position. Needle engaging member 70 is disassociated from surgical needle 12 while needle engaging member 68 is engaged and securely holds surgical needle 12 within recess 26 in jaw 16. Lock member 88 has engaged lock notch 102 thereby preventing rotation of toggle wheel 76 to secure surgical needle 12 in jaw 16.

In summary, in the above described manner, surgical needle 12 is initially secured and firmly held within jaw 18. Upon closure of jaws 18 and 16 due to pressure on handle members 30, surgical needle 12 is securely contained within recesses 26 and 28 and needle engaging members 68 and 70 are automatically reciprocated to transfer control of surgical needle 12 to jaw 16. Thus, surgical needle 12 is automatically transferred from jaw 18 to jaw 16 upon full closure of the handles without additional effort or manipulations on the part of the user.

Referring now to FIGS. 9–12, to reverse the sequence, i.e. pass surgical needle from jaw 16 back to jaw 18, handle members 30 are again moved to the closed position to initially close jaws 16 and 18. Thus, cam actuating lever 66 again performs the dual sequential functions of causing release leg 102 to disengage lock member 88 from lock notch 102 (FIG. 10) and cause toggle leg 110 to engage angled cam surface 98 and ledge 100 to initiate rotation of toggle wheel 60 in a counterclockwise direction (FIG. 11).

Counterclockwise rotation of toggle wheel 76 retracts needle engaging member 68 out of engagement with surgical needle 12 and advances needle engaging member 70 into engagement with surgical needle 12 in a manner similar to that described above. Knock off pin 106 also cams release leg 108 away from lock member 88. Thus, upon complete counterclockwise rotation of toggle wheel 76, lock member 88 will again engage lock notch 104 thereby securing surgical needle 12 back within recess 28 in jaw 18. Upon release of handle members 30, jaws 16 and 18 are again opened and apparatus 10 again holds surgical needle 12 within jaw 18 (FIG. 12). Pins 54 are again positioned within jaws closing segments 90. In this manner surgical needle 12 may be repeatedly and automatically passed back and forth between jaws 16 and 18 upon closure of handle member 30 and securely held within recesses 26 and 28 in jaws 16 and 18 when jaws 16 and 18 are moved to an open position. Thus, surgical needle 12 is under the total and precise control of an operator during an entire suturing operation without risk of needle 12 being released.

FIGS. 13A through 13I provide a detailed illustration of the use of vascular suturing apparatus 10 to attach a pair of vascular tissue sections endoscopically, e.g. by insertion of apparatus 10 through a trocar cannula T as shown in FIG. 1A. The operation of apparatus 10 is best described in terms of suturing open or free ends of vessels to form an end-to-end anastomosis procedure. It will be appreciated by those skilled in the art that a similar procedure and operation of apparatus 10 is readily applicable to suture an open end of a vascular tissue section to an incision in a side of a second vascular tissue second to form an end to side anastomosis or to suture the sides of vascular tissue sections to form a side to side anastomosis.

In order to facilitate discussion of the anastomosis procedure, the operation of vascular suturing apparatus 10 will be described solely in terms of jaws 16 and 18, and their respective recesses 26 and 28, of suturing apparatus 10 along with surgical needle 12 and associated length of suture material 14. However, it will be appreciated that the intricate working operations of vascular suturing apparatus 10 are performed in a manner described hereinabove. For example, the passing of surgical needle 12 between jaws 16 and 18 is accomplished in the same manner as previously described and will not be repeated herein.

FIG. 13A shows a pair of vascular tissue sections or vessels A and B. As noted hereinabove, suturing of vascular tissue sections endoscopically is typically accomplished within a reduced field of view. Thus, the following operation will be described as being performed within a restricted field of view indicated by circular line D as would be the case when viewed through an endoscope. Ends A1 and B1 of vascular tissue sections A and B, respectively, are prepared in known fashion to ensure that clean and undamaged tissues are sutured together.

In order to form surfaces through which surgical needle 12 can readily be inserted, ends A1 and B1 are preferably everted or spread open in known fashion to create everted edges A2 and B2 in vessels A and B, respectively (FIG. 13B).

Vessels A and B are approximated to bring everted edges A2 and B2 into an abutting relationship as shown in FIG. 13C. At this point vascular suturing apparatus 10 is inserted into the body cavity through cannula T (FIG. 1A) in known manner and is brought within the field of view by manipulating jaws 16 and 18, respectively, adjacent everted edges A2–B2. As shown, preferably, surgical needle 12 and associated length of suture material 14, initially contained within jaw 18 are positioned adjacent one side of everted edges A2–B2 while jaw 16 is positioned adjacent an opposite edge of everted edges A2–B2.

Jaws 16 and 18 are closed together to insert needle 12 through everted edges A2–B2 and enter into recess 26 in the opposite jaw 16 (FIG. 13D). At this point continued operation of vascular suturing apparatus 10 causes control of surgical needle 12 to be automatically transferred from jaw 18 to jaw 16. Additionally, as jaws 16 and 18 are closed about evened edges A2–B2, a working gap E is maintained between jaws 16 and 18 to prevent undesired compression or even crashing of everted edges A2–B2 of vascular tissue sections A and B.

Upon opening of jaws 16 and 18, (FIG. 13E) surgical needle 12 is securely held within jaw 16 and is drawn through, along with a portion of length of suture material 14, the everted edges A2–B2 of vessels A and B. In this manner, vessels A and B have been pierced and thereby have a suture stitch formed therein.

Referring to FIG. 13F, once length of suture material 14 has been at least partially drawn through both everted edges A2–B2, length of suture material 14 may be tied off to form a single stitch in edges A2–B2. Alternatively, jaws 16 and 18 may be closed in a manner described hereinabove to repass or transfer control of surgical needle 12 from jaw 16 back to jaw 18 and thus reposition the point of surgical needle 12 to again pierce tissue and form another stitch.

Thereafter, jaws 16 and 18 may be opened with needle 12 securely held within jaw 18 and again positioned on opposite sides of everted edges A2–B2 to form another stitch (FIG. 13G). Thus, continued repetition of the above described procedure win form a series of overlapping stitches through everted edges A2–B2 as best illustrated in FIGS. 13H and 13I.

Thus, it is possible in the above described manner to suture or pass a length of suture material through a vascular tissue section by positioning a surgical needle securely held within a first jaw adjacent the vascular tissue section to be sutured and closing the first jaw adjacent a second jaw. The needle may then subsequently be transferred to the second jaw and opened to draw the surgical needle and length of suture material through the tissue section. This procedure may be repeated to perform a series of stitches in a single vascular tissue section or to join two or more tissue vascular tissue sections together, for example, in end-to-side, side to side or end-to-end in anastomosis procedures. The above described operation occurs automatically upon full closure of the handles and no further manipulations on the part of the operator are required to transfer the surgical needle from one jaw to another.

While the present discussion contemplates piercing two vascular tissue sections upon a single closure of apparatus 10, it is well within the knowledge of those skilled in the art to suture vascular tissue sections by piercing a single vascular tissue section with needle 12 at a time and drawing suture material 14 therethrough. Thus, in extremely delicate procedures it is possible to insert a portion of length of suture material 14 within only a single vascular tissue at a time to suture a pair of vascular tissue sections together.

The above description of surgical suturing apparatus 10, its method of operation, and the various methods of suturing vascular tissues best illustrate the preferred embodiments and methods associated with vascular suturing apparatus 10. However, as noted above, a double pointed surgical needle, or surgical incision member as described in U.S. patent application Ser. No. 08/260,579, may be utilized which will allow suturing in both directions without having to repass a single pointed surgical needle and suture back to an opposing jaw to form another stitch. Further, as will be appreciated by those skilled in the art, various alternate jaw configurations along with alternate needle engaging member or needle engaging member configurations may be provided to facilitate suturing of various vascular tissues.

The following alternate jaw and needle engaging member configurations and embodiments are suitable for use in vascular suturing apparatus 10 and will be described merely in terms of the jaw and needle engaging member interactions and engagements along with surgical needle 12 and length of suture material 14.

FIGS. 14A and 14B present a first alternate embodiment of a jaw configuration 120 and needle engaging member 122. Jaw 120 is similar to jaws 16 and 18 described hereinabove and generally includes an enlarged bore 124 for receipt of a surgical needle 12. Bore 125 aids in positioning and transferring surgical needle 12 between jaws especially when pushed through tough tissue sections which may cause deflection of surgical needle 12. Bore 124 includes a V-shaped notch 126 at a distal end which cooperates with a V-shaped camming edge 128 on needle engaging member 122. Thus, as shown in FIG. 14B, upon distal movement of needle engaging member 122, V-shaped camming edge 128 cams surgical needle 12 within bore 124 against notch 126 to securely hold surgical needle 12 therein. As noted above, surgical needle 12 may be either smooth sided or notched adjacent an edge to receive at least a portion of V-shaped camming edge 128 of needle engaging member 122.

FIGS. 15A–15D illustrate another alternate jaw 130 and needle engaging member 132 configuration which utilizes proximal retraction, rather than distal advancement, of needle engaging member 132 to securely hold surgical needle 12 against jaw 130. Jaw 130 includes a V-shaped engagement notch 134 formed on the distal end while needle engaging member 132 contains an elongated slot 136 for receipt of surgical needle 12 therein. Referring to FIG. 15B, as needle engaging member 132 is retracted, surgical needle 12 disposed within slot 136 is cammed against and securely held within notch 134 in arm 130. As further shown in FIGS. 15C–15D, needle engaging member 132 may be formed from a shape memory alloy to be flexible and bent to initially hold surgical needle 12 within slot 136 and parallel to a longitudinal axis of jaw 130 to facilitate insertion through a cannula. As shown in FIG. 15D, upon exit of a cannula, needle engaging member assumes a deployed and unbent configuration.

FIGS. 16A and 16B illustrate yet another alternate embodiment of a jaw 138 and needle engaging member 140 configuration best suited for securing a U-shaped, half-circle or otherwise relatively hollow surgical needle 142 which preferably has engagement structure in the form of an engagement hole 144 formed therethrough. Surgical needle 142 (FIG. 16C) may have various cross-sectional configurations while still having suitable engagement structure in the form of hole 144. Jaw 138 has a bore 146 formed therein and needle engaging member 140 has a projecting tip 148 which preferably corresponds to the interior shape of the surgical needle 142. Needle engaging member 140 is further formed with a point or finger 150 formed on tip 148 and which is specifically designed to engage the engagement structure or hole 144 in surgical needle 142. Thus, upon positioning of surgical needle 142 within recess 146, distal advancement of needle engaging member 140 causes finger 150 to engage hole 144 and securely hold surgical needle 142 within jaw 138.

Referring now to FIGS. 17A and 17B, another alternate jaw 152 and needle engaging member 154 is shown for securely holding a round or otherwise preferably solid cross-sectional surgical needle 12. Jaw 152 preferably includes an angled forward edge 156 and a groove or slot 158 proximal to angled forward edge 156. Needle engaging member 154 also includes an angled forward edge 160 and a camming member 162 formed at a distal most portion of angled edge 160. Thus, referring to FIG. 17B, upon retraction of needle engaging member 154 camming member 162 forces surgical needle 12 into recess slot 158 thereby securing surgical needle 12 within jaw 152.

Figure 19A:
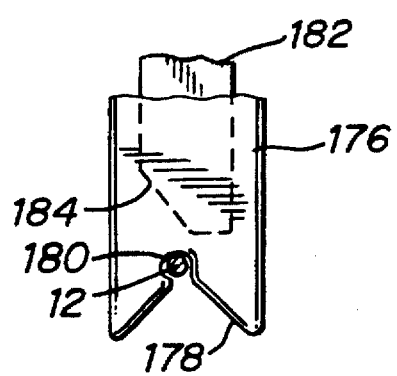
FIGS. 19A and 19B are enlarged side views of an alternate distal end and needle engaging member configuration designed for easy loading of a surgical needle.
Figure 19B:
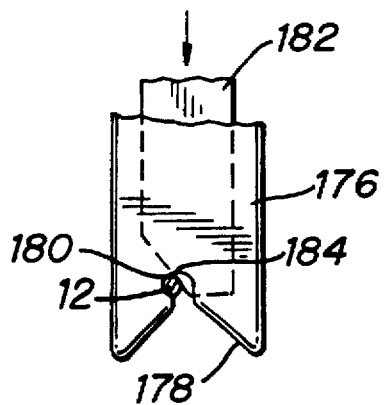

While the above described jaw and needle engaging member configurations include enclosed recesses or holes through which surgical needle 12 may be perpendicularly inserted, it may often be desirable to provide open ended or easy loading structure which will allow surgical needle 12 to be inserted parallel rather than perpendicular to the jaw structure. One particularly suitable jaw structure is illustrated in FIG. 19A and 19B. Jaw 176 is preferably formed with a V-shaped needle guiding recess 178 having a relatively round or circular needle receiving portion 180 at the apex of the V. Thus, needle 12 can be inserted into recess 170 from the distal end of jaw 176, i.e., parallel to its longitudinal axis, rather the moving surgical needle 12 perpendicularly to jaw 176 to enter an enclosed recess. Needle engaging member 182 includes an angled surface 184 which, when advanced as shown in FIG. 19B, cams against surgical needle 12 to firmly hold surgical needle 12 within circular recess 180 of jaw 176. It will particularly appreciated that the easy load style of jaw configurations and needle engaging member configurations are particularly suited to parallel moving jaw structure which may either move perpendicular to the longitudinal axis of a surgical needle, that is, slide parallel to each other or may move parallel to the longitudinal axis of a surgical needle, i.e., that is, move perpendicular with respect to each other. They are also particularly suited where the user wants to change needles either outside or inside the body cavity during the surgical procedure. The needle can be easily slid out of the recess and replaced with a different needle.

Figure 20A:
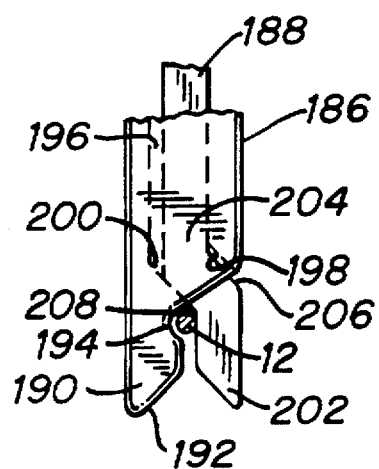
FIGS. 20A and 20B are enlarged side views of an alternate easy load style distal end and needle engaging member configuration.
Figure 20B:
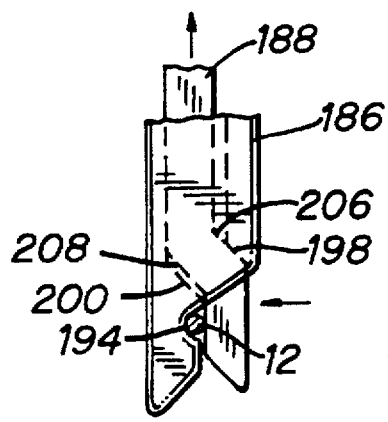

Referring now to FIGS. 20A and 20B, there is disclosed a further alternate easy load style jaw distal end and needle engaging member configuration. Jaw 186 preferably includes a single, distally extending hook 190 having an angled needle guiding from surface 192 and small semicircular recess 194 disposed distally of angled needle guiding front surface 192. Additionally, a channel 196 for receipt of needle engaging member 188 includes a pair of angled camming surfaces 198 and 200. Needle engaging member 188 includes a distally extending camming finger 202 having a dog leg connecting portion 204 which connects finger 202 to the remainder of needle engaging member 188. Dog leg portion 204 has camming edges 206 and 208 which cooperate with camming edges 198, 200, respectively, in jaw 186. As best shown in FIG. 20B, as needle engaging member 188 is retracted, camming edge 206 abuts camming edge 198 to move finger 202 sideways forcing surgical needle 12 to be firmly held within recess 194 in jaw 186. Similarly, distal advancement of needle engaging member 188 results in abutting camming edge 200 of jaw 188 to engage cam edge 208 to again move finger 202 sideways away from recess 194 thereby releasing surgical needle 12 from jaw 186.

Figure 21A:
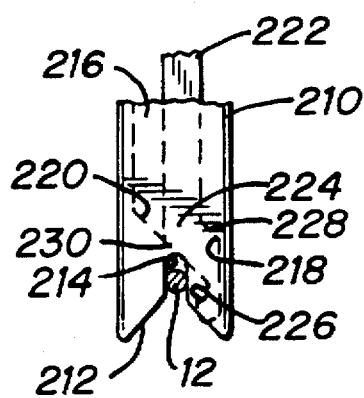
FIGS. 21A and 21B are enlarged side views of still another alternate easy load style distal end and needle engaging member configuration.
Figure 21B:
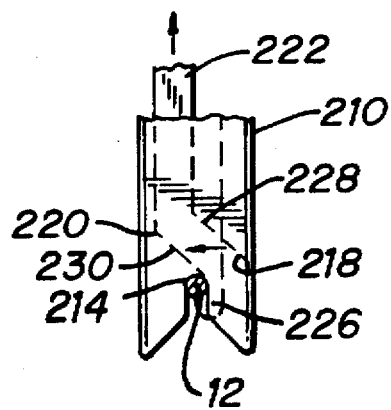

FIGS. 21A and 21B illustrate a further alternate embodiment of an easy load style jaw and needle engaging member configuration. Jaw 210 preferably includes a V-shaped needle guiding distal end 212 terminating in an elongated slot or recess 214 for receipt of surgical needle 12 therein. Preferably, jaw 210 has an elongated needle engaging member channel 216 having angled edges 218 and 220. Needle engaging member 222 also includes a dog leg end portion 224 similar to that described with respect to the embodiment disclosed in FIGS. 20A and 20B and contains a hook or recess edge 226 at the distalmost end thereof. Thus, as shown in FIG. 21B, upon proximal retraction of needle engaging member 222, a camming edge 228 on needle engaging member 222 engages angled edge 218 on jaw 210 to move needle engaging member 222 sideways thereby capturing surgical needle 12 within recess 214 by curved finger or hook 226. Similarly, distal advancement of needle engaging member 222 within channel 216 causes a camming edge 230 on needle engaging member 222 to engage angled edge 220 on jaw 210 to move hook 226 away from recess 214 thereby releasing surgical needle 12 from jaw 210.

Figure 18:
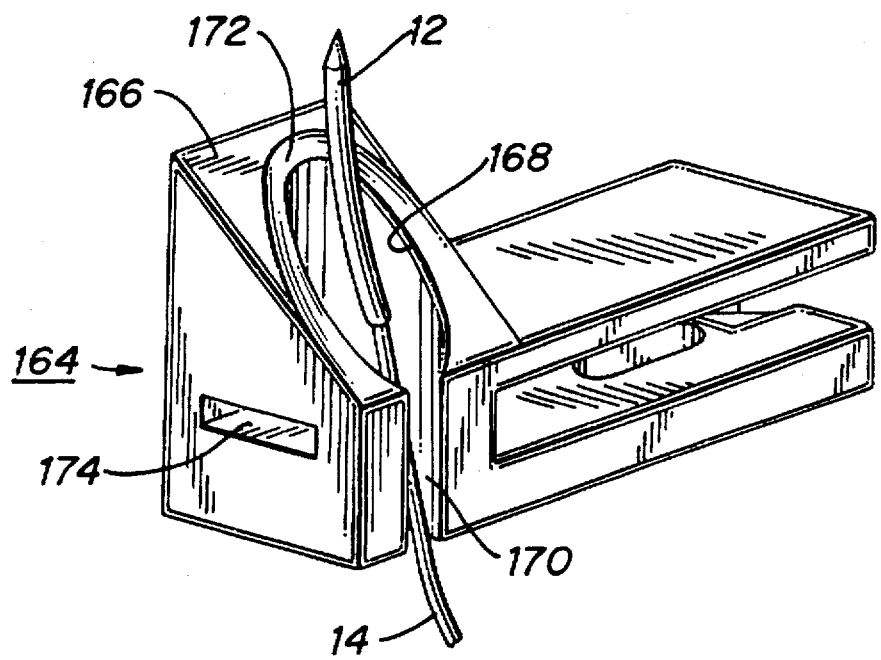
FIG. 18 is an enlarged perspective view of an alternate distal end slotted for ease in manipulation of a length of suture affixed to a surgical needle.

FIG. 18 illustrates an alternate jaw structure particularly suited for use with a single pointed surgical needle 12 having an associated length of suture material 14 extending from an opposite end of the point. Jaw 164 is configured to manage and manipulate suture material 14 such that it does not interfere with the transfer of surgical needle 12 between an opposing jaw similar to jaw 16. Preferably, jaw 164 includes angular inwardly sloped portion 166 having a recess 168 therethrough. Recess 168 has a slot 170 along one edge thereof to allow suture material 14 to pass therethrough. Additionally, angled portion 166 is further formed with a chamfered or channeling surface 172 which serves to guide suture material 14 through slot 170 and into recess 168. In this manner, when surgical needle 12 is passed back and forth between the jaws, such as for example, jaws 164 and 16, the suture will be prevented from tangling Additionally, the chamfered surface 172, by guiding the suture material 14 through the slot, keeps the suture out of the way of the needle engaging member extending through slot 174. By forming slot 174 through jaw 164, a distal end of a needle engaging member may abut surgical needle 12 to hold it within recess 168 or, alternatively, a side edge of needle engaging member may cam against an edge of surgical needle 12 to hold it within recess 168. Jaw 164 may be removable or, alternatively, integral with the remainder of its associated jaw.

Figure 22A:
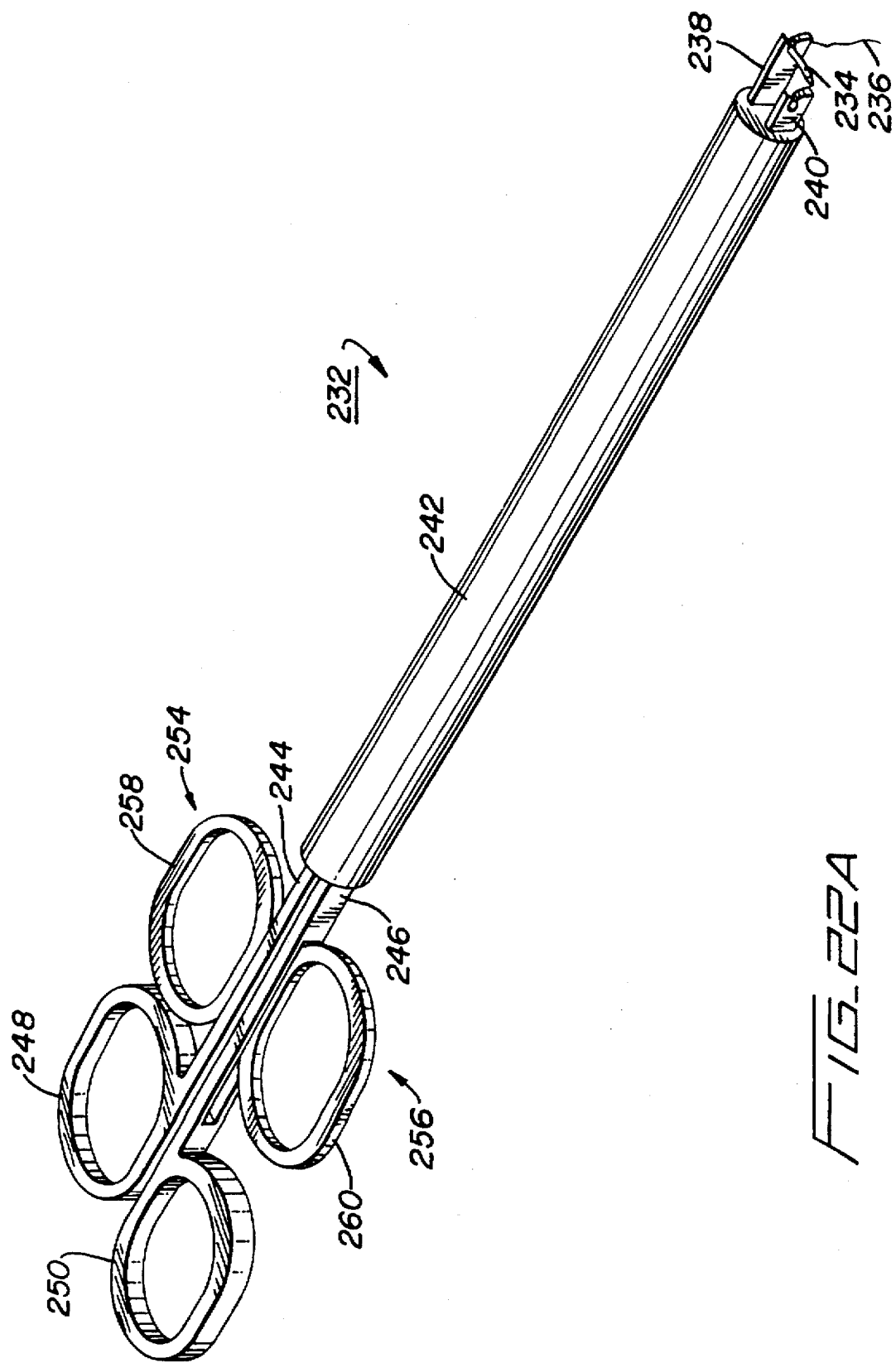
FIG. 22A is a perspective view of parallel moving jaw embodiment of a vascular surgical suturing apparatus.
Figure 22B:
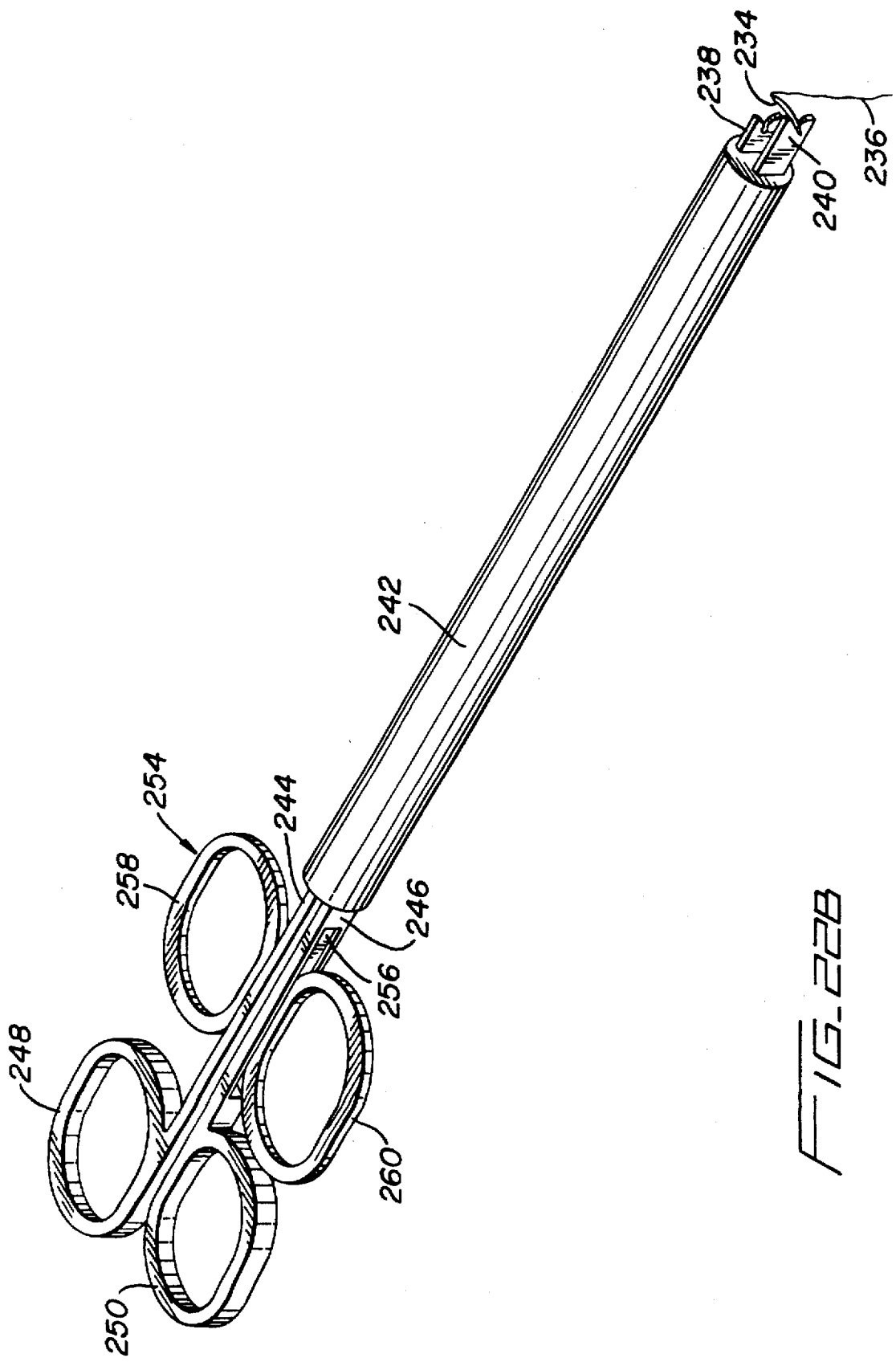
FIG. 22B is a perspective view similar to FIG. 22A with the surgical needle having been passed to the opposing jaw.

Referring now to FIGS. 22A and 22B, there is disclosed an alternate vascular surgical suturing apparatus particularly designed for suturing vascular tissue sections in endoscopic or laparoscopic procedures. Apparatus 232 is specifically configured to operate with the easy load style jaw and needle engaging member configurations discussed above. Notably, apparatus 232 utilities jaw structure which moves in a direction parallel to their respective axis in order to minimize instrument movement within a body cavity. Apparatus 232 is particularly suited for use with a surgical needle such as, for example, surgical needle 234 having an associated length of suture material 236 attached thereto.

As noted hereinabove, apparatus 232 utilizes easy load jaw structure such as, for example, first jaw 238 which is substantially similar to jaw 210 described hereinabove and has a second jaw 240 which is also similar to jaw 210 described hereinabove. While apparatus 232 is illustrated has having an identical first and second jaw structure 238 and 240 respectively, it is also contemplated to utilize differing easy load style jaw and needle engaging member configurations to facilitate various operations.

Apparatus 232 generally includes a tubular housing or body portion 242 having first and second jaw control arms 244 and 246 extending therethrough. Distal ends of control arms 244 and 246, respectively, are affixed to proximal ends of first and second jaws 238 and 240. First and second finger loops 248 and 250 are affixed to the respective proximal ends of jaw control arms 244, 246. Additionally, first and second jaw control arms 244 and 246 each include first and second needle engaging member control arms 254 and 256, respectively. Thus, by moving finger loops 248, 250 first and second jaws 238 and 240 are reciprocated in parallel fashion. By moving control arms 254, 256 the needle engaging member structure of first and second jaws 248 and 250 are reciprocated.

More specifically, first needle engaging member control arm 254 has a finger loop 258 and, similarly, second needle engaging member control arm 256 has a finger loop 260. Needle engaging member control arms 254 and 256 reciprocate within slots in the jaw control arms 244 and 246.

Referring specifically to FIG. 22A, it can be seen that a first jaw control arm 244 is in a distalmost position holding a surgical needle 234 within first jaw 238. As noted hereinabove, jaw 238 is of the tension easy load variety and thus finger loop 258 and needle engaging member control arm 254 are in a proximalmost position to grasp surgical needle 234 within first jaw 238. Transfer of surgical needle 234 from first jaw 238 to second jaw 240 may be accomplished in one of two ways. First jaw control arm 244 could be retracted proximally to a position where second jaw 240 can grasp surgical needle 244 or alternatively second jaw control arm 246 could be extended distally to a position where second jaw 240 is again in a position to grasp surgical needle 234.

Referring to FIG. 22B, first jaw control arm 244 had been retracted while first needle engaging member control arm 254 had been advanced to release surgical needle 234 from first jaw 238. Simultaneously, second jaw control arm 246 had been advanced to distal position and second needle engaging member control arm 256 has been retracted to grasp surgical needle 234 within second jaw 240. In this manner, surgical needle 234 may be repeatedly passed back and forth between first and second jaws 238 and 240 with little or no movement outside the diameter of body portion 242. Preferably body portion 242 is on the order of 5 to 12 millimeters in diameter to facilitate use within cannulas.

It will be understood that various modifications may be made to the embodiments disclosed herein. For example, as noted hereinabove, parallel movement along or perpendicular to the jaw axes is contemplated as well as straight and/of double pointed surgical needles such as surgical incision members. Further, other methods of grasping a surgical needle within a single jaw are contemplated. Additionally, modifications within the skill of those knowledgeable in the are may be made to the camming and reciprocating mechanisms to facilitate automatic transfer of a surgical needle from one jaw to another. Therefore, the above description should not be construed as limiting, but merely as exemplifications as preferred embodiments. Those skilled in the art will envision other modifications within the scope and spirit of the claims appended hereto.

What is claimed is:

1. An endoscopic apparatus for suturing tissue comprising:
   a) an elongated tubular housing;
   b) a first jaw and a second jaw mounted for movement on a distal end of the tubular housing and remotely actuable for movement between an open position and a closed position wherein the first and second jaws are in close cooperative alignment;
   c) a handle mechanism including a handle member, the handle mechanism associated with the proximal end of the tubular housing, the handle member being actuable to move the first and second jaws between the open and closed positions;
   d) a reciprocating mechanism, mounted to the handle mechanism, remote from the first and second jaws and movable between a first position securing a surgical needle within one of the first and second jaws and a second position releasing the surgical needle from the same one of the first and second jaws; and
   e) a cam actuating lever engagable with the reciprocating mechanism to cam the reciprocating mechanism between the first and second positions in response to a predetermined movement of the handle member.

2. The apparatus according to claim 1, wherein the cam actuating lever is positioned with respect to the reciprocating mechanism such that the cam actuating lever automatically engages the reciprocating mechanism subsequent to closure of the jaws.

3. The apparatus according to claim 1 wherein, the first and second jaws have respective first and second needle engaging members and the reciprocating mechanism is operatively associated with the first and second needle engaging members for alternatively moving the first and second needle engaging members into and out of engagement with a surgical needle subsequent to closure of the first and second jaws.

4. The apparatus according to claim 3, wherein the reciprocating mechanism includes a toggle wheel rotatably mounted adjacent a proximal portion of the tubular housing with a proximal end of each of the first and second needle engaging members being connected to opposite sides of the toggle wheel such that rotation of the toggle wheel simultaneously retracts one of the first and second needle engaging members and advances the other of the first and second needle engaging members.

5. The apparatus according to claim 4, wherein the cam actuating lever is mounted on the handle member, such that movement of the handle member drives the cam actuating lever into engagement with camming surfaces on the toggle wheel to rotate the toggle wheel upon movement of the first and second jaw handle member into the closed position.

6. The apparatus according to claim 3, wherein the first jaw has a first recess for receipt of a portion of a surgical needle therein, the first needle engaging member movable adjacent the first recess to engage the surgical needle disposed therein.

7. The apparatus according to claim 1, further comprising a lockout member engagable with the reciprocating mechanism and mounted for movement between a locked position blocking movement of the reciprocating mechanism and an unlocked position allowing movement of the reciprocating mechanism.

8. The apparatus according to claim 7, wherein the cam actuating lever includes a release leg, the release leg moving the lockout member from the locked position to the unlocked position upon closure of the handle member.

9. An endoscopic apparatus for suturing tissue comprising:
   a) an elongated tubular housing;
   b) a first and a second jaw mounted for movement adjacent a distal end of the tubular housing and remotely actuable for movement between an open position and a closed position wherein the first and second jaws are in close cooperative alignment;
   c) a handle member operatively associated with the proximal end of the tubular housing and actuable to move the first and second jaws between the open and closed positions;
   d) a reciprocating mechanism operatively associated with the handle member remote from the first and second jaws and movable between a first position securing a surgical needle within one of the first and second jaws and a second position releasing the surgical needle from the same one of the first and second jaws;
   e) a cam actuating lever engagable with the reciprocating mechanism to cam the reciprocating mechanism between the first and second positions in response to a predetermined movement of the handle member: and
   f) a handle portion positioned adjacent a proximal end of the tubular housing, the handle portion including a plate mounted within the handle portion, the plate including camming structure for moving the jaws from the open position to the closed position and subsequently moving the cam actuating lever into camming engagement with the reciprocating mechanism.

10. The apparatus of claim 9, wherein said camming structure includes a cam slot and the handle member includes a cam pin mounted for movement in the cam slot for sequencing movement of the jaws and the reciprocating mechanism.

11. An apparatus for suturing tissue comprising:
   a) an elongated tubular housing;
   b) a handle mechanism including a pair of handles mounted adjacent a proximal end of the tubular housing;
   c) a first jaw extending from the elongated tubular housing and having a first needle receiving recess configured to receive a portion of a surgical needle therein and a first needle engaging member mounted for movement with respect to the first jaw;
   d) a second jaw mounted adjacent the housing for movement with respect to the first jaw and having a second needle receiving recess configured to receive a portion of a surgical needle therein, the second jaw having a second needle engaging member mounted for movement with respect to the second jaw;
   e) a reciprocating mechanism mounted to the handle mechanism and connected to the first and second needle engaging members, the reciprocating mechanism actuable by the handles for alternately moving the first and second needle engaging members into and out of the first and second needle receiving recesses, the reciprocating mechanism being movable by the handles between a first position advancing the first needle engaging member with respect to the first jaw and a second position advancing the second needle engaging member with respect to the second jaw; and
   f) a cam actuating lever operatively associated with the handles, the cam actuating lever automatically camming the reciprocating mechanism between the first and second positions to allow transfer of control of a surgical needle between the first and second jaws upon closure of the handles.

12. The apparatus according to claim 11, wherein the reciprocating mechanism includes a toggle wheel rotatably affixed to the tubular housing and having first and second camming surfaces such that an initial closure of the handles forces the cam actuating lever into engagement with the first camming surface to automatically move the toggle wheel to the first position and a subsequent closure of the handles forces the cam actuating lever into engagement with the second camming surface to automatically move the toggle wheel to the second position.

13. An apparatus for suturing tissue endoscopically comprising:
   a) an elongated body portion defining a longitudinal axis;
   b) a first needle holding jaw mounted for movement parallel to the longitudinal axis and having a first needle engaging surface;
   c) a second needle holding jaw mounted for movement parallel to the longitudinal axis and having a second needle engaging surface; and
   d) a securing mechanism, longitudinally movable relative to the elongated body portion and the first and second needle engaging surfaces, for holding a needle in one of the first and second needle holding jaws, the securing mechanism and the first and second needle holding jaws being relatively longitudinally movable wherein the needle is held substantially perpendicular to the longitudinal axis, the needle being transferable between the first and second needle holding jaws.

14. The apparatus according to claim 13, further comprising a control member for sliding the securing mechanism between a first position to secure the surgical needle within the respective jaw and a second position to release the surgical needle from the jaw.

15. The apparatus according to claim 13, wherein the securing mechanism is engageable with the needle.

16. The apparatus according to claim 15, wherein the needle is secured between an edge of the needle securing mechanism and at least one of the first and second needle engaging surfaces.

17. The apparatus according to claim 13, wherein at least one of the first and second jaws has a substantially planar surface.

18. The apparatus according to claim 17, wherein the planar surface is oriented substantially perpendicular to a longitudinal axis of the needle.

19. The apparatus according to claim 13, wherein the securing mechanism has a substantially planar surface adjacent the needle.

20. The apparatus according to claim 13, wherein at least one of the first and second jaws has an opening for receipt of the needle.

21. The apparatus according to claim 20, wherein the opening is a bore formed in at least one of the first and second jaws.

22. The apparatus according to claim 20, wherein the opening is a slot fomed in at least one of the first and second jaws.

23. The apparatus according to claim 20, wherein the opening is a notch formed in at least one of the first and second jaws.

24. A method of endoscopically suturing vascular tissue comprising the steps of:
   a) providing an endoscopic suturing apparatus having first and second needle holding jaws mounted to the body portion and pivotal relative to each other about a common pivot point, the first and second jaws movable relative to the body portion from a first position spaced apart to a second position in close cooperative alignment;
   b) endoscopically accessing a surgical site containing vascular tissue to be sutured;
   c) preparing the vascular tissue for suturing by manipulating adjacent portions of the vascular tissue to form a tissue area suitable for suturing;
   d) inserting a portion of the body portion of the endoscopic suturing apparatus to the surgical site including the first and second needle holding jaws with a surgical needle and associated length of suture held in the first needle holding jaw;
   e) positioning the first and second needle holding jaws and surgical needle in the first position adjacent the formed tissue area;
   f) remotely actuating the endoscopic suturing apparatus to close both the first and second jaws about the common pivot point to the second position with the formed tissue area therebetween to drive the surgical needle through the formed tissue area;
   g) transferring the surgical needle from the first jaw to the second jaw by actuating a camming mechanism positioned in a proximal end of the endoscopic suturing apparatus;
   h) remotely actuating the endoscopic suturing apparatus to open the jaws to the first position; and
   i) drawing the length of suture at least partially through the formed tissue area to form a stitch therein.

25. The method of claim 24, wherein the step of endoscopically accessing a surgical site includes inserting a cannula to provide access to vascular tissue by the endoscopic suturing apparatus.

26. The method of claim 25, wherein the step of remotely actuating the apparatus to open the jaws and the step of transferring the surgical needle from the first jaw to the second jaw comprises the step of actuating a handle mechanism.

27. The method of claim 26, wherein the step of actuating the handle mechanism includes the step of camming a reciprocating mechanism positioned in the apparatus to move a needle securing mechanism to secure the needle in the second jaw.

28. The method of claim 27, wherein the step of moving the needle securing mechanism to secure the needle in the second jaw includes the step of simultaneously releasing the needle from the first jaw.

29. A method of endoscopically suturing vascular tissue comprising the steps of:
 a) providing an endoscopic suturing apparatus having an elongated body portion and first and second needle holding jaws mounted to the body portion, the first and second jaws relatively movable from a first position spaced apart to a second position in close cooperative alignment;
 b) endoscopically accessing a surgical site containing vascular tissue to sutured;
 c) preparing the vascular tissue for suturing by manipulating adjacent portions of the vascular tissue to form a tissue area suitable for suturing;
 d) inserting a portion of the body portion of the endoscopic suturing apparatus to the surgical site including the first and second needle holding jaws with a surgical needle and associated length of suture held in the first needle holding jaw;
 e) positioning the first and second needle holding jaws and surgical needle in the first position adjacent the formed tissue area;
 f) remotely actuating the endoscopic suturing apparatus to close both the first and second jaws to the second position with the formed tissue area therebetween to drive the surgical needle through the formed tissue area;
 g) transferring the surgical needle from the first jaw to the second jaw by actuating a camming mechanism positioned in a proximal end of the endoscopic suturing apparatus to move securing members extending through the length of the elongated body portion relative to the surgical needle;
 h) remotely actuating the endoscopic suturing apparatus to open the jaws to the first position; and
 i) drawing the length of suture at least partially through the formed tissue area to form a stitch therein.

30. The method according to claim 29, wherein the step of remotely actuating the endoscopic suturing apparatus to close both the first and second jaws to the second position includes moving both the first jaw and the second jaw relative to the other.

* * * * *